US007547681B2

(12) United States Patent
Scholler et al.

(10) Patent No.: US 7,547,681 B2
(45) Date of Patent: *Jun. 16, 2009

(54) SURFACE RECEPTOR ANTIGEN VACCINES

(75) Inventors: Nathalie B Scholler, Seattle, WA (US);
Mary L Disis, Renton, WA (US);
Ingegerd Hellstrom, Seattle, WA (US);
Karl Erik Hellstrom, Seattle, WA (US)

(73) Assignee: University of Washington, Seattle, WA (US)

( * ) Notice: Subject to any disclaimer, the term of this patent is extended or adjusted under 35 U.S.C. 154(b) by 736 days.

This patent is subject to a terminal disclaimer.

(21) Appl. No.: 10/762,128

(22) Filed: Jan. 20, 2004

(65) Prior Publication Data
US 2004/0219161 A1 Nov. 4, 2004

Related U.S. Application Data

(63) Continuation of application No. 09/441,411, filed on Nov. 16, 1999, now Pat. No. 6,734,172.

(60) Provisional application No. 60/109,106, filed on Nov. 18, 1998.

(51) Int. Cl.
*A01N 43/04* (2006.01)
*A61K 31/70* (2006.01)
*C12N 15/00* (2006.01)

(52) U.S. Cl. .................. 514/44; 435/320.1
(58) Field of Classification Search ............. 514/44; 435/320.1
See application file for complete search history.

(56) References Cited

U.S. PATENT DOCUMENTS

| 5,478,556 | A | 12/1995 | Elliott et al. ............ 424/852 |
| 5,571,711 | A | 11/1996 | Van der Bruggen et al. ...... 435/240.2 |
| 5,596,090 | A | 1/1997 | Hoke et al. ............ 435/6 |
| 5,683,886 | A | 11/1997 | Van der Bruggen et al. ...... 435/7.24 |
| 5,891,432 | A | 4/1999 | Hoo ............ 424/93.21 |
| 6,348,450 | B1 * | 2/2002 | Tang et al. ............ 514/44 |

FOREIGN PATENT DOCUMENTS

| EP | 0668350 A1 | 8/1995 |
| GB | 2241703 | 9/1991 |
| JP | 9-75090 | 3/1991 |
| WO | WO 96/11279 | 4/1996 |
| WO | WO 96/40039 | 12/1996 |
| WO | WO 98/08947 | 3/1998 |

OTHER PUBLICATIONS

Babiuk et al. (2003) Induction of immune responses by DNA vaccines in large animals. Vaccine 21: 649-658.*
Finn, OJ (2003) Cancer vaccines: Between the idea and the reality. Nature Reviews Immunology 3: 630-641.*
Leitner et al. (2000) DNA and RNA-based vaccines: Principles, progress and prospects. Vaccine 18: 765-777.*
McCluskie et al. (1999) Route and method of delivery of DNA vaccine influence immune responses in mice and non-human primates. Molecular Medicine 5: 287-300.*
Adema et al., "Molecular Characterization of the Melanocyte Lineage-Specific Antigen gp100," *The Journal of Biological Chemistry* 269(31):20126-20133, 1994.
Banchereau, "Interleukin-4," in Angus W. Thomson (ed.), *The Cytokine Handbook*, Academic Press Limited, California, 1991, pp. 119-148.
Bargmann et al., "Multiple Independent Activations of the *neu* Oncogene by a Point Mutation Altering the Transmembrane Domain of p185," *Cell* 45:649-657, 1986.
Barnd et al., "Specific, Major Histocompatibility Complex-Unrestricted Recognition of Tumor-Associated Mucins by Human Cytotoxic T Cells," *Proc. Natl. Acad. Sci. USA* 86:7159-7163, 1989.
Baselga et al., "Recombinant Humanized Anti-HER2 Antibody (Herceptin™) Enhances the Antitumor Activity of Paclitaxel and Doxorubicin Against HER2/*neu* Overexpressing Human Breast Cancer Xenografts," *Cancer Research* 58:2825-2831, 1981.
Bier et al., "Anti-(Epidermal Growth Factor) Receptor Monoclonal Antibodies for the Induction of Antibody-Dependent Cell-Mediated Cytotoxicity Against Squamous Cell Carcinoma Lines of the Head and Neck," *Cancer Immunol. Immunother.* 46:167-173, 1998.
Borriello et al., "Differential Expression of Alternate mB7-2 Transcripts," *Journal of Immunology* 155(12):5490-5497, 1995.
Buonavista et al., "DNA Immunization with a Combination of Rat Neu Antigen, CD86, and 4-IBB Ligand Results in the Generation of HER-2/neu (HER-2) Antigodies in Neu Transgenic Mice," *Cancer Gene Therapy* 5(6):S2, Abstract No. O-5, 1998.
Conry et al., "Selected strategies to augment polynucleotide immunization," *Gene Therapy* 3(1):67-74, Jan. 1996.
DeGrado et al., "Sequence and Structural Homologies Among Type I and Type II Interferons," *Nature* 300(25):379-381, 1982.
Disis et al., "Existent T-Cell and Antibody Immunity of HER-2/neu Protein in Patients with Breast Cancer," *Cancer Research* 54:16-20, 1991.
Donnelly et al., "DNA Vaccines," *Annual Review of Immunology* 15(1):617-648, 1997.
Eck et al., *Goodman's and Gilman's the Pharmacological Basis of Therapeutics*,McGraw-Hill, New York, 1996 "Gene Based Therapy," pp. 77-101.
Ehrenfeld and Semler, "Anatomy of the Poliovirus Internal Ribosome Entry Site," *Current Topics in Microbiology and Immunology* 203:66-83, 1995.
Emtage et al., "Enhanced Interleukin-2 Gene Transfer Immunotherapy of Breast Cancer by Coexpression of B7-1 and B7-2," *Journal of Interferon and Cytokine Research* 18(11):927-937, 1998.

(Continued)

*Primary Examiner*—Ann-Marie Falk
(74) *Attorney, Agent, or Firm*—Christensen O'Connor Johnson Kindness PLLC

(57) ABSTRACT

The invention provides compositions and methods directed to cell surface receptor antigen specific vaccines. More specifically, vaccines are provided that induce or enhance host antibody titers specific for cell surface receptor antigens and that include recombinant expression constructs containing nucleic acids encoding a target cell surface receptor antigen and one or more immune response altering molecules, or the expressed products themselves.

11 Claims, 3 Drawing Sheets

OTHER PUBLICATIONS

Figure 1:
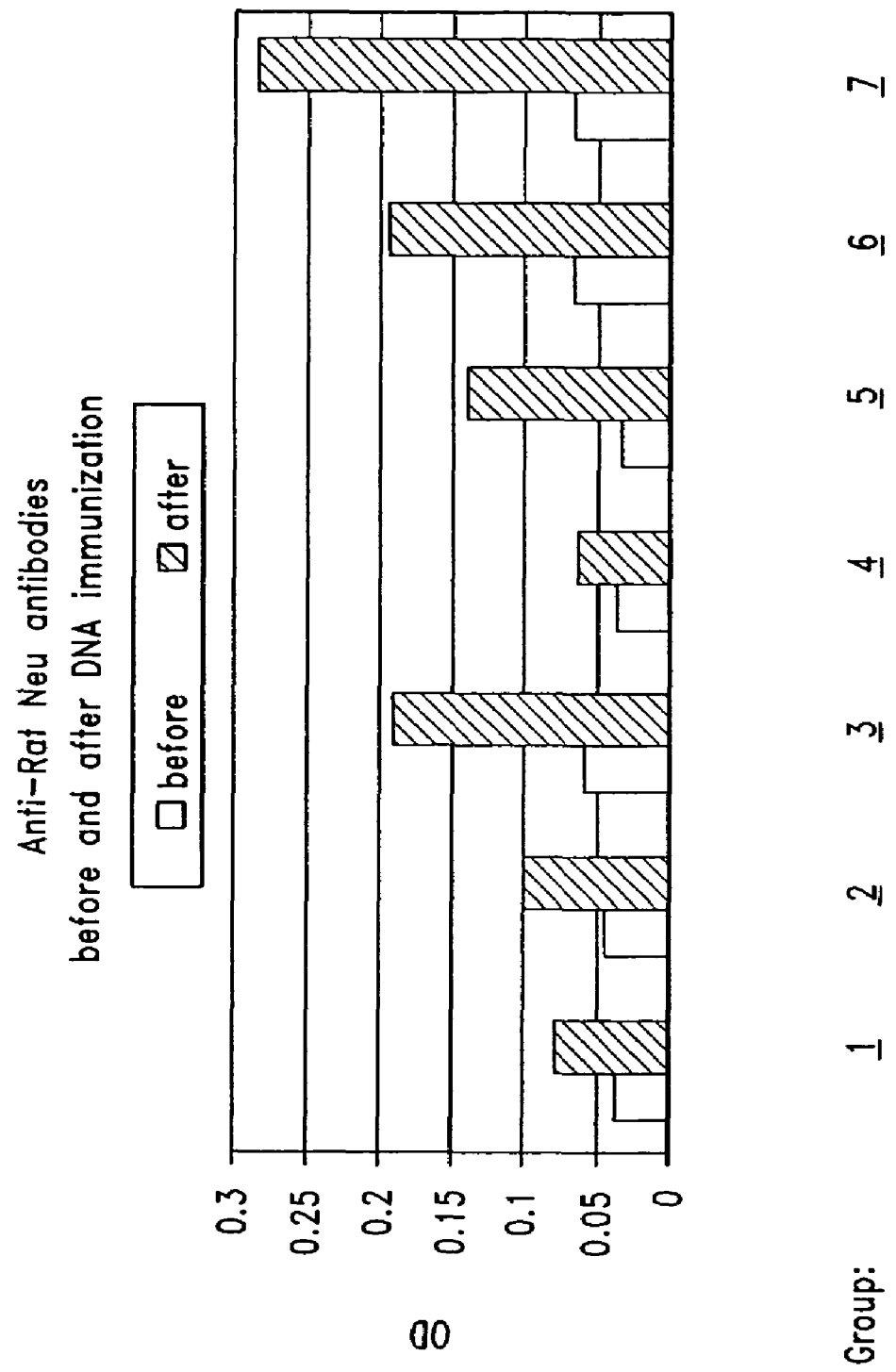

Farrar and Schreiber, "The Molecular Cell Biology of Interferon-γ and Its Receptor," *Annu. Rev. Immunol.* 11:571-611, 1993.

Freeman et al., "B7, A New Member of the Ig Superfamily with Unique Expression on Activated and Neoplastic B Cells," *J. of Immunol.* 143(8):2714-1722, 1989.

Freeman et al., "Murine B7-2, and Alternative CTLA4 Counter-Receptor that Costimulates T Cell Proliferation and Interleukin 2 Production," *J. Exp. Med.* 178:2185-2192, 1993.

Freeman et al., "Structure, Expression, and T Cell Costimulatory Activity of the Murine Homologue of the Human B Lymphocyte Activation Antigen B7," *J. Exp. Med.* 174:625-631, 1991.

Gertsmayer, B. et al., "Costimulation of T Cell Proliferation by a Chimeric B7-2 Antibody Fusion Protein Specifically Targeted to Cells Expressing the Erbb2 Proto-Oncogene," *J. Immunol.* 158(10):4585-90, May 1997.

Gold and Freedman, "Demonstration of Tumor-Specific Antigens in Human Colonic Carcinomata by Immunological Tolerance and Absorption Techniques," *J. Exp. Med.* 121(3):439-462, plate 35-plate 39, 1965.

Goodwin et al., "Molecular Cloning of a Ligand for the Inducible T Cell Gene 4-1BB: A Member of an Emerging Family of Cytokines with Homology to Tumor Necrosis Factor," *Eur. J. Immunol.* 23:2631-2641, 1993.

Gray et al., "Expression of Human Immune Interferon cDNA in *E. coli* and Monkey Cells," *Nature* 295:503-508, 1982.

Greene et al., "Covalent Dimerization of CD28/CTLA-4 and Oligomerization of CD80/CD86 Regulate T Cell Costimulatory Interactions," *The Journal of Biological Chemistry* 271(43):26762-26771, 1996.

Hellström and Hellström, "T Cell Immunity of Tumor Antigens," *Critical Reviews in Immunology* 18:1-6, 1998.

Hoffman et al., "Antitumor Activity of Anti-Epidermal Growth Factor Receptor Monoclonal Antibodies and Cisplatin in Ten Human Head and Neck Squamous Cell Carcinoma Lines," *Anticancer Research* 17:4419-4426, 1997.

June et al., "Role of the CD28 Receptor in T-Cell Activation," *Immunol. Today* 11:211-216, 1990.

Kawakami et al., "Cloning of the Gene Coding for a Shared Human Melanoma Antigen Recognized by Autologous T Cells Infiltrating Into Tumour," *Proc. Nat. Acad. Sci. USA* 91:3515-3519, 1994.

Keegan et al., "The Interleukin-4 Receptor: Signal Transduction by a Hematopoietin Receptor," *J. Leukocyt. Biol.* 55:272-279, 1994.

Kim et al., "Development of a Multicomponent Candidate Vaccine for HIV-1," *Vaccine* 15(8):879-883, 1997.

Kwon and Weissman, "cDNA Sequences of Two Inducible T-Cell Genes," *Proc. Nat. Acad. Sci. USA* 86:1963-1967, 1989.

Li et al., "Costimulation by CD48 and B7-1 Induces Immunity Against Poorly Immunogenic Tumors," *J. Exp. Med.* 183:639-644, 1996.

Linsley et al., "CD28 Engagement by B7/BB-1 Induces Transient Down-Regulation of CD28 Synthesis and Prolonged Unresponsiveness to CD28 Signaling," *J. Immunol.* 150(8):3161-3169, 1993.

Linsley et al., "Human B7-1 (CD80) and B7-2 (CD86) Bind with Similar Avidites but Distinct Kinetics to CD28 and CTLA-4 Receptors," *Immunity* 1:793-801, 1994.

Liu, "Vaccine Developments," *Nature Medicine Vaccine Supplement* 4(5):515-519, 1998.

Melero et al., "Amplification of Tumor Immunity by Gene Transfer of the Co-Stimulatory 4-1BB Ligand: Synergy with the CD28 Co-Stimulatory Pathway," *Eur. J. Immunol* 28:1116-1121, 1998.

Pardoll, "Cancer Vaccines," *Nature Medicine Vaccine Supplement* 4(5):525-531, 1998.

Petit et al., "Neutralizing Antibodies Against Epidermal Growth Factor and ErbB-2/*neu* Receptor Tyrosine Kinases Down-Regulate Vascular Endothelial Growth Factor Production by Tumor Cells In Vitro and In Vivo," *American Journal of Pathology* 151(6):1523-1530, 1997.

Pietras et al., "Antibody to HER-2/*neu* Receptor Blocks DNA Repair After Cisplatin in Human Breast and Ovarian Cancer Cells," *Oncogene* 9:1829-1838, 1994.

Plowman et al., "Heregulin Induces Tyrosine Phosphorylation of HER4/p180*erbB4*," *Nature* 366:473-475, 1993.

Rees et al., "Bicistronic Vector for the Creating of Stable Mammalian Cell Lines that Predisposes All Antibiotic-Resistant Cells to Express Recombinant Protein," *Biotechniques* 20(1):102-109, 1996.

Reiter and Rapport, "Dual Effects of Cytokines in Regulation of MHC-Unrestricted Cell Mediated Cytotoxicity," *Crit. Rev. Immunol.* 13(1):1-34, 1993.

Rinderknecht et al., "Natural Human Interferon-γ," *J. Biol. Chem.* 259(11):6790-6797, 1984.

Schlom and Hodge, "The diversity of T-cell co-stimulation in the induction of antitumor immunity," *Immunological Reviews* 170:73-84, Aug. 1999.

Sugimoto et al., "Efficient Expression of Drug-Selectable Genes in Retroviral Vectors Under Control of an Internal Ribosome Entry Site," *Bio/Technology* 12:694-698, 1994.

Tascon et al. "Polynucleotide Vaccination Induces a Significant Protective Immune Response against Mycobacteria," *Vaccines* 96:45-49, 1996.

Topalian et al., "Human CD4+ T Cells Specifically Recognize a Shared Melanoma-Associated Antigen Encoded by the Tyrosine Gene," *Proc. Nat. Acad. Sci. USA* 91:9461-9465, 1994.

Trowbridge and Omary, "Human Cell Surface Glycoprotein Related to Cell Proliferation is the Receptor for Transferrin," *Proc. Nat. Acad. USA* 78(5):3039-3043, 1981.

Udayachander et al., "Anti-Tumor Activity of Monoclonal Antibody CIBCNSH3 Generated to the Human EGF Receptor," *Hum. Antibodies* 8 (2):60-64, 1997, abstract only.

van den Bruggen et al., "A Gene Encoding an Antigen Recognized by Cytolytic T Lymphocytes on a Human Melanoma," *Science* 254:1643-1647, 1991.

Verma, I. et al., "Gene Therapy —Promises, Problems and Prospects," *Nature* 389(6648):239-42, Sep. 1997.

Wang and Siddiqui, "Structure and Function of the Hepatitis C Virus Internal Ribosome Entry Site," *Curr. Top. Microbiol. Immunol* 203:99-115, 1995.

Weber et al., "Tumor Immunity and Autoimmunity Induced by Immunization with Homologous DNA," *J. Clin. Invest* 102:1258-1264, 1998.

Yoshino et al., "Association of HER2/neu Expression with Sensitivity to Tumor-Specific CTL in Human Ovarian Cancer," *J. Immunol.* 152:2393-2400, 1994.

Zitvogel et al., "Interleukin-12 and B7.1 Co-Stimulation Cooperate in the Induction of Effective Antitumor Immunity and Therapy of Established Tumors," *Eur. J. Immunol.* 26:1335-1341, 1996.

* cited by examiner

SEQUENCE LISTING

<160> NUMBER OF SEQ ID NOS: 26

<210> SEQ ID NO 1
<211> LENGTH: 29
<212> TYPE: DNA
<213> ORGANISM: Artificial Sequence
<220> FEATURE:
<223> OTHER INFORMATION: PCR primer

<400> SEQUENCE: 1
ctaagcttat ggcttgcaat tgtcagttg                                          29

<210> SEQ ID NO 2
<211> LENGTH: 29
<212> TYPE: DNA
<213> ORGANISM: Artificial Sequence
<220> FEATURE:
<223> OTHER INFORMATION: PCR primer

<400> SEQUENCE: 2
gtatcgatct aaaggaagac ggtctgttc                                          29

<210> SEQ ID NO 3
<211> LENGTH: 27
<212> TYPE: DNA
<213> ORGANISM: Artificial Sequence
<220> FEATURE:
<223> OTHER INFORMATION: PCR primer

<400> SEQUENCE: 3
cgaagcttgt tccagaactt acggaag                                            27

<210> SEQ ID NO 4
<211> LENGTH: 26
<212> TYPE: DNA
<213> ORGANISM: Artificial Sequence
<220> FEATURE:
<223> OTHER INFORMATION: PCR primer

<400> SEQUENCE: 4
cgatcgatct ttcctcaggc tctcac                                             26

<210> SEQ ID NO 5
<211> LENGTH: 4473
<212> TYPE: DNA
<213> ORGANISM: Homo sapiens

<400> SEQUENCE: 5
aaggggaggt aaccctggcc cctttggtcg gggccccggg cagccgcgcg ccccttccca        60
cggggccctt tactgcgccg cgcgcccggc ccccacccct cgcagcaccc gcgccccgc        120 gccctcccag ccgggtccag ccggagccat ggggccggag ccgcagtgag caccatggag       180
ctggcggcct tgtgccgctg ggggctcctc ctcgccctct tgccccccgg agccgcgagc       240
acccaagtgt gcaccggcac agacatgaag ctgcggctcc ctgccagtcc cgagacccac       300
ctggacatgc tccgccacct ctaccagggc tgccaggtgg tgcagggaaa cctggaactc       360
acctacctgc ccaccaatgc cagcctgtcc ttcctgcagg atatccagga ggtgcagggc       420
tacgtgctca tcgctcacaa ccaagtgagg caggtccac tgcagaggct gcggattgtg       480
cgaggcaccc agtctctttga ggacaactat gccctggccg tgctagacaa tggagacccg       540
ctgaacaata ccacccctgt cacaggggcc tccccaggag gcctgcggga gctgcagctt       600

```
cgaagcctca cagagatctt gaaaggaggg gtcttgatcc agcggaaccc ccagctctgc    660
taccaggaca cgattttgtg gaaggacatc ttccacaaga caaccagct ggctctcaca     720 ctgatagaca ccaaccgctc tcgggcctgc caccctgtt ctccgatgtg taagggctcc     780
cgctgctggg gagagagttc tgaggattgt cagagcctga cgcgcactgt ctgtgccggt    840
ggctgtgccc gctgcaaggg gccactgccc actgactgct gccatgagca gtgtgctgcc    900
ggctgcacgg gccccaagca ctctgactgc ctggcctgcc tccacttcaa ccacagtggc    960
atctgtgagc tgcactgccc agccctggtc acctacaaca cagacacgtt tgagtccatg   1020
cccaatcccg agggccggta tacattcggc gccagctgtg tgactgcctg tccctacaac   1080
tacctttcta cggacgtggg atcctgcacc ctcgtctgcc ccctgcacaa ccaagaggtg   1140
acagcagagg atggaacaca gcggtgtgag aagtgcagca agccctgtgc ccgagtgtgc   1200
tatggtctgg gcatggagca cttgcgagag gtgagggcag ttaccagtgc caatatccag   1260
gagtttgctg gctgcaagaa gatctttggg agcctggcat ttctgccgga gagctttgat   1320
ggggacccag cctccaacac tgccccgctc cagccagagc agctccaagt gtttgagact   1380
ctggaagaga tcacaggtta cctatacatc tcagcatggc cggacagcct gcctgacctc   1440
agcgtcttcc agaacctgca gtaatccgg ggacgaattc tgcacaatgg cgcctactcg    1500
ctgaccctgc aagggctggg catcagctgg ctggggctgc gctcactgag ggaactgggc   1560
agtggactgg ccctcatcca ccataacacc cacctctgct tcgtgcacac ggtgccctgg   1620
gaccagctct ttcggaaccc gcaccaagct ctgctccaca ctgccaaccg gccagaggac   1680
gagtgtgtgg gcgagggcct ggcctgccac cagctgtgcg cccgagggca ctgctggggt   1740
ccagggccca cccagtgtgt caactgcagc cagttccttc ggggccagga gtgcgtggag   1800
gaatgccgag tactgcaggg gctccccagg gagtatgtga atgccaggca ctgtttgccg   1860
tgccaccctg agtgtcagcc ccagaatggc tcagtgacct gttttggacc ggaggctgac   1920
cagtgtgtgg cctgtgccca ctataaggac cctcccttct gcgtggcccg ctgccccagc   1980
ggtgtgaaac ctgacctctc ctacatgccc atctggaagt ttccagatga ggagggcgca   2040
tgccagcctt gccccatcaa ctgcacccac tcctgtgtgg acctggatga caagggctgc   2100
cccgccgagc agagagccag ccctctgacg tccatcatct ctgcggtggt tggcattctg   2160
ctggtcgtgg tcttgggggt ggtctttggg atcctcatca gcgacggca gcagaagatc   2220 cggaagtaca cgatgcggag actgctgcag gaaacggagc tggtggagcc gctgacacct   2280
agcggagcga tgcccaacca ggcgcagatg cggatcctga aagagacgga gctgaggaag   2340
gtgaaggtgc ttggatctgg cgcttttggc acagtctaca agggcatctg gatccctgat   2400
ggggagaatg tgaaaattcc agtggccatc aaagtgttga gggaaaacac atcccccaaa   2460
gccaacaaag aaatcttaga cgaagcatac gtgatggctg tgtgggctc cccatatgtc   2520 tcccgccttc tgggcatctg cctgacatcc acggtgcagc tggtgacaca gcttatgccc   2580
tatggctgcc tcttagacca tgtccgggaa aaccgcggac gctgggctc ccaggacctg   2640 ctgaactggt gtatgcagat tgccaagggg atgagctacc tggaggatgt gcggctcgta   2700
cacagggact tggccgctcg gaacgtgctg gtcaagagtc caaccatgt caaaattaca   2760 gacttcgggc tggctcggct gctggacatt gacgagacag agtaccatgc agatgggggc   2820
aaggtgccca tcaagtggat ggcgctggag tccattctcc gccggcgtt cacccaccag   2880 agtgatgtgt ggagttatgg tgtgactgtg tgggagctga tgactttgg ggccaaacct   2940
```

```
tacgatggga tcccagcccg ggagatccct gacctgctgg aaaaggggga gcggctgccc    3000
cagcccccca tctgcaccat tgatgtctac atgatcatgg tcaaatgttg gatgattgac    3060
tctgaatgtc ggccaagatt ccgggagttg gtgtctgaat ctcccgcat ggccagggac    3120 ccccagcgct ttgtggtcat ccagaatgag gacttgggcc cagccagtcc cttggacagc    3180
accttctacc gctcactgct ggaggacgat gacatggggg acctggtgga tgctgaggag    3240
tatctggtac cccagcaggg cttcttctgt ccagaccctg ccccgggcgc tggggggcatg   3300 gtccaccaca gcaccgcag ctcatctacc aggagtggcg gtggggacct gacactaggg     3360 ctggagcct ctgaagagga ggcccccagg tctccactgg caccctccga aggggctggc     3420
tccgatgtat ttgatggtga cctgggaatg ggggcagcca aggggctgca aagcctcccc    3480
acacatgacc ccagccctct acagcggtac agtgaggacc ccacagtacc cctgccctct    3540
gagactgatg gctacgttgc ccccctgacc tgcagccccc agcctgaata tgtgaaccag    3600
ccagatgttc ggccccagcc cccttcgccc cgagagggcc ctctgcctgc tgcccgacct    3660
gctggtgcca ctctggaaag gcccaagact ctctccccag ggaagaatgg ggtcgtcaaa    3720
gacgtttttg cctttggggg tgccgtggag aaccccgagt acttgacacc ccagggagga    3780
gctgcccctc agccccaccc tcctcctgcc ttcagcccag ccttcgacaa cctctattac    3840
tgggaccagg acccaccaga gcgggggct ccacccagca ccttcaaagg gacacctacg     3900
gcagagaacc cagagtacct gggtctggac gtgccagtgt gaaccagaag gccaagtccg    3960
cagaagccct gatgtgtcct cagggagcag ggaaggcctg acttctgctg gcatcaagag    4020
gtgggagggc cctccgacca cttccagggg aacctgccat gccaggaacc tgtcctaagg    4080
aaccttcctt cctgcttgag ttcccagatg gctggaaggg gtccagcctc gttggaagag    4140
gaacagcact ggggagtctt tgtggattct gaggccctgc caatgagac tctagggtcc     4200 agtggatgcc acagcccagc ttggcccttt ccttccagat cctgggtact gaaagcctta    4260
gggaagctgg cctgagaggg gaagcggccc taagggagtg tctaagaaca aaagcgaccc    4320
attcagagac tgtccctgaa acctagtact gccccccatg aggaaggaac agcaatggtg    4380
tcagtatcca ggctttgtac agagtgcttt tctgtttagt ttttactttt tttgttttgt    4440 tttttaaag atgaaataaa gacccagggg gag                                  4473
```

<210> SEQ ID NO 6
<211> LENGTH: 1255
<212> TYPE: PRT
<213> ORGANISM: Homo sapiens

<400> SEQUENCE: 6

```
Met Glu Leu Ala Ala Leu Cys Arg Trp Gly Leu Leu Ala Leu Leu
 1               5                  10                  15

Pro Pro Gly Ala Ala Ser Thr Gln Val Cys Thr Gly Thr Asp Met Lys
                 20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
```

-continued

```
                100                 105                 110
Ala Leu Ala Val Leu Asp Asn Gly Asp Pro Leu Asn Thr Thr Pro
            115                 120                 125
Val Thr Gly Ala Ser Pro Gly Gly Leu Arg Glu Leu Gln Leu Arg Ser
    130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
            195                 200                 205
Ser Glu Asp Cys Gln Ser Leu Thr Arg Thr Val Cys Ala Gly Gly Cys
    210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
            275                 280                 285
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
    355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
            515                 520                 525
```

```
Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
930                 935                 940
```

```
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
            965                 970                 975
Ser Arg Met Ala Arg Asp Pro Gln Arg Phe Val Val Ile Gln Asn Glu
        980                 985                 990
Asp Leu Gly Pro Ala Ser Pro Leu Asp Ser Thr Phe Tyr Arg Ser Leu
    995                 1000                1005
Leu Glu Asp Asp Asp Met Gly Asp Leu Val Asp Ala Glu Glu Tyr Leu
    1010                1015                1020
Val Pro Gln Gln Gly Phe Phe Cys Pro Asp Pro Ala Pro Gly Ala Gly
1025                1030                1035                1040
Gly Met Val His His Arg His Arg Ser Ser Thr Arg Ser Gly Gly
                1045                1050                1055
Gly Asp Leu Thr Leu Gly Leu Glu Pro Ser Glu Glu Ala Pro Arg
                1060                1065                1070
Ser Pro Leu Ala Pro Ser Glu Gly Ala Gly Ser Asp Val Phe Asp Gly
        1075                1080                1085
Asp Leu Gly Met Gly Ala Ala Lys Gly Leu Gln Ser Leu Pro Thr His
    1090                1095                1100
Asp Pro Ser Pro Leu Gln Arg Tyr Ser Glu Asp Pro Thr Val Pro Leu
1105                1110                1115                1120
Pro Ser Glu Thr Asp Gly Tyr Val Ala Pro Leu Thr Cys Ser Pro Gln
        1125                1130                1135
Pro Glu Tyr Val Asn Gln Pro Asp Val Arg Pro Gln Pro Pro Ser Pro
        1140                1145                1150
Arg Glu Gly Pro Leu Pro Ala Ala Arg Pro Ala Gly Ala Thr Leu Glu
        1155                1160                1165
Arg Pro Lys Thr Leu Ser Pro Gly Lys Asn Gly Val Val Lys Asp Val
    1170                1175                1180
Phe Ala Phe Gly Gly Ala Val Glu Asn Pro Glu Tyr Leu Thr Pro Gln
1185                1190                1195                1200
Gly Gly Ala Ala Pro Gln Pro His Pro Pro Ala Phe Ser Pro Ala
                1205                1210                1215
Phe Asp Asn Leu Tyr Tyr Trp Asp Gln Asp Pro Pro Glu Arg Gly Ala
        1220                1225                1230
Pro Pro Ser Thr Phe Lys Gly Thr Pro Thr Ala Glu Asn Pro Glu Tyr
        1235                1240                1245
Leu Gly Leu Asp Val Pro Val
    1250                1255

<210> SEQ ID NO 7
<211> LENGTH: 729
<212> TYPE: DNA
<213> ORGANISM: Drosophila melanogaster

<400> SEQUENCE: 7
gcatttccag agggctacct cacgtcctgc tccttcgact atctttcgga caactttgac      60
acccggttgt tgtgggcac catcttcttt ttcagcttcg tgtgtcccac gctgatgatc     120
ctttactact actcgcagat cgtgggccat gtcttcagcc acgaaaaggc cctacgggag     180
caggccaaga aaatgaacgt ggagtcgctg cgctccaatg tggacaagag caaggagacg     240
gcggagatac ggattgcgaa ggcggctatc accatctgct cctgttcttc gtgtcgtgg     300 acgccctacg gcgtaatgtc gctgatcggg gcattcgggg ataagagtct gcttacacaa     360
```

```
ggagccacga tgatcccggc ctgcacctgc aaactggtgg cgtgcataga cccattcgtc      420
tatgccataa gtcaccccag ataccgcttg gagctgcaga agcgctgtcc ctggctggga      480
gtcaacgaaa agtctgggga gatctcttcg gcgcagtcca cgaccaccca ggagcagcaa      540
cagactaccg ctgcatagaa ccaaggacaa ctctactcta agacaactga ccatgtaaca      600
tgaaagccaa ggaaaaagta taaaatgccg acaacgaaac tgtataacat taattttata      660
atttgtagtg tgacattctt gagtttgaaa taaataaata gtaacttatt gcaaacgaag      720
tagaaaatg                                                              729
```

```
<210> SEQ ID NO 8
<211> LENGTH: 378
<212> TYPE: PRT
<213> ORGANISM: Drosophila melanogaster

<400> SEQUENCE: 8

Met Glu Pro Leu Cys Asn Ala Ser Glu Pro Pro Leu Arg Pro Glu Ala
 1               5                  10                  15

Arg Ser Ser Gly Asn Gly Asp Leu Gln Phe Leu Gly Trp Asn Val Pro
            20                  25                  30

Pro Asp Gln Ile Gln Tyr Ile Pro Glu His Trp Leu Thr Gln Leu Glu
        35                  40                  45

Pro Pro Ala Ser Met His Tyr Met Leu Gly Val Phe Tyr Ile Phe Leu
    50                  55                  60

Phe Cys Ala Ser Thr Val Gly Asn Gly Met Val Ile Trp Ile Phe Ser
65                  70                  75                  80

Thr Ser Lys Ser Leu Arg Thr Pro Ser Asn Met Phe Val Leu Asn Leu
                85                  90                  95

Ala Val Phe Asp Leu Ile Met Cys Leu Lys Ala Pro Ile Phe Asn Ser
            100                 105                 110

Phe His Arg Gly Phe Ala Ile Tyr Leu Gly Asn Thr Trp Cys Gln Ile
        115                 120                 125

Phe Ala Ser Ile Gly Ser Tyr Ser Gly Ile Gly Ala Gly Met Thr Asn
    130                 135                 140

Ala Ala Ile Gly Tyr Asp Arg Tyr Asn Val Ile Thr Lys Pro Met Asn
145                 150                 155                 160

Arg Asn Met Thr Phe Thr Lys Ala Val Ile Met Asn Ile Ile Ile Trp
                165                 170                 175

Leu Tyr Cys Thr Pro Trp Val Val Leu Pro Leu Thr Gln Phe Trp Asp
            180                 185                 190

Arg Phe Val Pro Glu Gly Tyr Leu Thr Ser Cys Ser Phe Asp Tyr Leu
        195                 200                 205

Ser Asp Asn Phe Asp Thr Arg Leu Phe Val Gly Thr Ile Phe Phe Phe
    210                 215                 220

Ser Phe Val Cys Pro Thr Leu Met Ile Leu Tyr Tyr Ser Gln Ile
225                 230                 235                 240

Val Gly His Val Phe Ser His Glu Lys Ala Leu Arg Glu Gln Ala Lys
                245                 250                 255

Lys Met Asn Val Glu Ser Leu Arg Ser Asn Val Asp Lys Ser Lys Glu
            260                 265                 270

Thr Ala Glu Ile Arg Ile Ala Lys Ala Ala Ile Thr Ile Cys Phe Leu
        275                 280                 285

Phe Phe Val Ser Trp Thr Pro Tyr Gly Val Met Ser Leu Ile Gly Ala
    290                 295                 300
```

```
Phe Gly Asp Lys Ser Leu Leu Thr Gln Gly Ala Thr Met Ile Pro Ala
305                 310                 315                 320

Cys Thr Cys Lys Leu Val Ala Cys Ile Asp Pro Phe Val Tyr Ala Ile
                325                 330                 335

Ser His Pro Arg Tyr Arg Leu Glu Leu Gln Lys Arg Cys Pro Trp Leu
            340                 345                 350

Gly Val Asn Glu Lys Ser Gly Ile Ser Ser Ala Gln Ser Thr Thr
        355                 360                 365

Thr Gln Glu Gln Gln Gln Thr Thr Ala Ala
    370                 375

<210> SEQ ID NO 9
<211> LENGTH: 191
<212> TYPE: PRT
<213> ORGANISM: Homo sapiens

<400> SEQUENCE: 9

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala
            180                 185                 190

<210> SEQ ID NO 10
<211> LENGTH: 1277
<212> TYPE: DNA
<213> ORGANISM: Homo sapiens

<400> SEQUENCE: 10
gtcatctgct attttaaaac ttccttggaa taatatatgt aatctacttc taataagttt      60
ttcttattta gcattttggt ctaaactaat ttataattat ttagccttat ttctccatgt     120
ttaacttgct ttaaagctca gcactggtgt tttcagccat ggcttctcca ttttaaggct     180
attttaattc atttattatt ctggaatata tccttaaata atttatttag gaaggctgtc     240
tgttgggtgg tatttctgtt gcagttgttg ttttcttgcc tgcttggtga catatttcta     300
ttgacttgac acttaactgg catcttatct aggtagaata tgctaattca aaattctgca     360
```

```
gatattggtc tgttgttttt tgccatttag ggttgagtaa gatgccaagt tggttttttgg      420 ttctctgtag tcattctgtt ttcattttgt ttttagcttt gcctttggaa tttaaaatgt      480
tcaaaatgat ttgtctggat gagaatcgat tttcataact tttgctttga tacactaaac      540
agtttgagtt tctagatgat gcccatttta attcatacga ggaaatatct tctagtatag      600
tttctgcttg attaattcta tgtttgtctc ttagggacat ctattaattt tataatgctg      660 ccttttttc agacttctgt ttcagaatat tcgctttcat gaatgtaatc cttggctata       720
gtaggaatga aataataaaa gcagtagctt ctgtctgccc tccttggtta tgcagtcctt      780
acagacattc tccccacctc ccatccccc accccagctc agtgaaactc tccacacttt       840
ggttgtggaa attggcaggg ttaggtggct actcactccc aatccacatc cacaataaat      900
cactttttat tatcttatca aaatctgtag aatgcctctt tattctattt tgttgctgcg      960
gaggtttgtt ttctctttct aattatttta ttttctaggt tttttgaggg aatttcaaga     1020
ggggagattt tttattcagg ctcatcttaa cgtcatgtct ggaactcaag ctactgaatt     1080
atatattctt taatacatat agacctacgt caatgagttt aaactgcaag gaaagggtta     1140
aatttcttcc tcaagtgtgg tcaaaatctg tagagaaaag aggaacagct tctcttaaag     1200
aaagttagct gggtaggtat acagtcattg ccgaggaagg cttgcacagg gtgaaagctt     1260
tgcttctctg ctgctgt                                                    1277
```

<210> SEQ ID NO 11
<211> LENGTH: 356
<212> TYPE: PRT
<213> ORGANISM: Mus musculus

<400> SEQUENCE: 11

```
Met Ala Lys Thr Ile Arg Arg Leu Ser Val Ala Phe Leu Thr Leu Ser
  1               5                  10                  15

Asp Arg Gly Pro His Tyr Lys Ile Leu Pro Leu Pro His Lys Gly
            20                  25                  30

Trp Thr Pro Gly Leu Thr His Asn Ala Ser Leu Tyr Cys Ala Ser Ile
        35                  40                  45

Ile Leu Lys Asn Thr Met Gly Leu Ala Ile Leu Ile Phe Val Thr Val
    50                  55                  60

Leu Leu Ile Ser Asp Ala Val Ser Val Glu Thr Gln Ala Tyr Phe Asn
65                  70                  75                  80

Gly Thr Ala Tyr Leu Pro Cys Pro Phe Thr Lys Ala Gln Asn Ile Ser
                85                  90                  95

Leu Ser Glu Leu Val Val Phe Trp Gln Asp Gln Gln Lys Leu Val Leu
            100                 105                 110

Tyr Glu His Tyr Leu Gly Thr Glu Lys Leu Asp Ser Val Asn Ala Lys
        115                 120                 125

Tyr Leu Gly Arg Thr Ser Phe Asp Arg Asn Asn Trp Thr Leu Arg Leu
    130                 135                 140

His Asn Val Gln Ile Lys Asp Met Gly Ser Tyr Asp Cys Phe Ile Gln
145                 150                 155                 160

Lys Lys Pro Pro Thr Gly Ser Ile Ile Leu Gln Gln Thr Leu Thr Glu
                165                 170                 175

Leu Ser Val Ile Ala Asn Phe Ser Glu Pro Glu Ile Lys Leu Ala Gln
            180                 185                 190

Asn Val Thr Gly Asn Ser Gly Ile Asn Leu Thr Cys Thr Ser Lys Gln
        195                 200                 205
```

```
Gly His Pro Lys Pro Lys Lys Met Tyr Phe Leu Ile Thr Asn Ser Thr
    210                 215                 220

Asn Glu Tyr Gly Asp Asn Met Gln Ile Ser Gln Asp Asn Val Thr Glu
225                 230                 235                 240

Leu Phe Ser Ile Ser Asn Ser Leu Ser Leu Ser Phe Pro Asp Gly Val
                245                 250                 255

Trp His Met Thr Val Val Cys Val Leu Glu Thr Glu Ser Met Lys Ile
            260                 265                 270

Ser Ser Lys Pro Leu Asn Phe Thr Gln Glu Phe Pro Ser Pro Gln Thr
        275                 280                 285

Tyr Trp Lys Glu Ile Thr Ala Ser Val Thr Val Ala Leu Leu Leu Val
    290                 295                 300

Met Leu Leu Ile Ile Val Cys His Lys Lys Pro Asn Gln Pro Ser Arg
305                 310                 315                 320

Pro Ser Asn Thr Ala Ser Lys Leu Glu Arg Asp Ser Asn Ala Asp Arg
                325                 330                 335

Glu Thr Ile Asn Leu Lys Glu Leu Glu Pro Gln Ile Ala Ser Ala Lys
            340                 345                 350

Pro Asn Ala Glu
        355

<210> SEQ ID NO 12
<211> LENGTH: 356
<212> TYPE: PRT
<213> ORGANISM: Mus musculus

<400> SEQUENCE: 12

Met Ala Lys Thr Ile Arg Arg Leu Ser Val Ala Phe Leu Thr Leu Ser
1               5                   10                  15

Asp Arg Gly Pro His Tyr Lys Ile Leu Leu Pro Leu Pro His Lys Gly
                20                  25                  30

Trp Thr Pro Gly Leu Thr His Asn Ala Ser Leu Tyr Cys Ala Ser Ile
            35                  40                  45

Ile Leu Lys Asn Thr Met Gly Leu Ala Ile Leu Ile Phe Val Thr Val
    50                  55                  60

Leu Leu Ile Ser Asp Ala Val Ser Val Glu Thr Gln Ala Tyr Phe Asn
65                  70                  75                  80

Gly Thr Ala Tyr Leu Pro Cys Pro Phe Thr Lys Ala Gln Asn Ile Ser
                85                  90                  95

Leu Ser Glu Leu Val Val Phe Trp Gln Asp Gln Gln Lys Leu Val Leu
            100                 105                 110

Tyr Glu His Tyr Leu Gly Thr Glu Lys Leu Asp Ser Val Asn Ala Lys
        115                 120                 125

Tyr Leu Gly Arg Thr Ser Phe Asp Arg Asn Asn Trp Thr Leu Arg Leu
    130                 135                 140

His Asn Val Gln Ile Lys Asp Met Gly Ser Tyr Asp Cys Phe Ile Gln
145                 150                 155                 160

Lys Lys Pro Pro Thr Gly Ser Ile Ile Leu Gln Gln Thr Leu Thr Glu
                165                 170                 175

Leu Ser Val Ile Ala Asn Phe Ser Glu Pro Glu Ile Lys Leu Ala Gln
            180                 185                 190

Asn Val Thr Gly Asn Ser Gly Ile Asn Leu Thr Cys Thr Ser Lys Gln
        195                 200                 205

Gly His Pro Lys Pro Lys Lys Met Tyr Phe Leu Ile Thr Asn Ser Thr
```

```
                210                 215                 220
Asn Glu Tyr Gly Asp Asn Met Gln Ile Ser Gln Asp Asn Val Thr Glu
225                 230                 235                 240

Leu Phe Ser Ile Ser Asn Ser Leu Ser Leu Ser Phe Pro Asp Gly Val
                245                 250                 255

Trp His Met Thr Val Val Cys Val Leu Glu Thr Glu Ser Met Lys Ile
                260                 265                 270

Ser Ser Lys Pro Leu Asn Phe Thr Gln Glu Phe Pro Ser Pro Gln Thr
            275                 280                 285

Tyr Trp Lys Glu Ile Thr Ala Ser Val Thr Val Ala Leu Leu Leu Val
        290                 295                 300

Met Leu Leu Ile Ile Val Cys His Lys Lys Pro Asn Gln Pro Ser Arg
305                 310                 315                 320

Pro Ser Asn Thr Ala Ser Lys Leu Glu Arg Asp Ser Asn Ala Asp Arg
                325                 330                 335

Glu Thr Ile Asn Leu Lys Glu Leu Glu Pro Gln Ile Ala Ser Ala Lys
                340                 345                 350

Pro Asn Ala Glu
        355

<210> SEQ ID NO 13
<211> LENGTH: 309
<212> TYPE: PRT
<213> ORGANISM: Mus musculus

<400> SEQUENCE: 13

Met Asp Pro Arg Cys Thr Met Gly Leu Ala Ile Leu Ile Phe Val Thr
1               5                   10                  15

Val Leu Leu Ile Ser Asp Ala Val Ser Val Glu Thr Gln Ala Tyr Phe
                20                  25                  30

Asn Gly Thr Ala Tyr Leu Pro Cys Pro Phe Thr Lys Ala Gln Asn Ile
            35                  40                  45

Ser Leu Ser Glu Leu Val Val Phe Trp Gln Asp Gln Gln Lys Leu Val
    50                  55                  60

Leu Tyr Glu His Tyr Leu Gly Thr Glu Lys Leu Asp Ser Val Asn Ala
65                  70                  75                  80

Lys Tyr Leu Gly Arg Thr Ser Phe Asp Arg Asn Asn Trp Thr Leu Arg
                85                  90                  95

Leu His Asn Val Gln Ile Lys Asp Met Gly Ser Tyr Asp Cys Phe Ile
                100                 105                 110

Gln Lys Lys Pro Pro Thr Gly Ser Ile Ile Leu Gln Gln Thr Leu Thr
            115                 120                 125

Glu Leu Ser Val Ile Ala Asn Phe Ser Glu Pro Glu Ile Lys Leu Ala
        130                 135                 140

Gln Asn Val Thr Gly Asn Ser Gly Ile Asn Leu Thr Cys Thr Ser Lys
145                 150                 155                 160

Gln Gly His Pro Lys Pro Lys Lys Met Tyr Phe Leu Ile Thr Asn Ser
                165                 170                 175

Thr Asn Glu Tyr Gly Asp Asn Met Gln Ile Ser Gln Asp Asn Val Thr
                180                 185                 190

Glu Leu Phe Ser Ile Ser Asn Ser Leu Ser Leu Ser Phe Pro Asp Gly
            195                 200                 205

Val Trp His Met Thr Val Val Cys Val Leu Glu Thr Glu Ser Met Lys
    210                 215                 220
```

```
Ile Ser Ser Lys Pro Leu Asn Phe Thr Gln Glu Phe Pro Ser Pro Gln
225                 230                 235                 240

Thr Tyr Trp Lys Glu Ile Thr Ala Ser Val Thr Val Ala Leu Leu Leu
            245                 250                 255

Val Met Leu Leu Ile Ile Val Cys His Lys Lys Pro Asn Gln Pro Ser
            260                 265                 270

Arg Pro Ser Asn Thr Ala Ser Lys Leu Glu Arg Asp Ser Asn Ala Asp
            275                 280                 285

Arg Glu Thr Ile Asn Leu Lys Glu Leu Glu Pro Gln Ile Ala Ser Ala
            290                 295                 300

Lys Pro Asn Ala Glu
305

<210> SEQ ID NO 14
<211> LENGTH: 314
<212> TYPE: PRT
<213> ORGANISM: Mus musculus

<400> SEQUENCE: 14

Met Tyr Val Ile Lys Thr Cys Ala Thr Cys Thr Met Gly Leu Ala Ile
1               5                   10                  15

Leu Ile Phe Val Thr Val Leu Leu Ile Ser Asp Ala Val Ser Val Glu
            20                  25                  30

Thr Gln Ala Tyr Phe Asn Gly Thr Ala Tyr Leu Pro Cys Pro Phe Thr
            35                  40                  45

Lys Ala Gln Asn Ile Ser Leu Ser Glu Leu Val Val Phe Trp Gln Asp
50                  55                  60

Gln Gln Lys Leu Val Leu Tyr Glu His Tyr Leu Gly Thr Glu Lys Leu
65                  70                  75                  80

Asp Ser Val Asn Ala Lys Tyr Leu Gly Arg Thr Ser Phe Asp Arg Asn
                85                  90                  95

Asn Trp Thr Leu Arg Leu His Asn Val Gln Ile Lys Asp Met Gly Ser
            100                 105                 110

Tyr Asp Cys Phe Ile Gln Lys Lys Pro Pro Thr Gly Ser Ile Ile Leu
            115                 120                 125

Gln Gln Thr Leu Thr Glu Leu Ser Val Ile Ala Asn Phe Ser Glu Pro
130                 135                 140

Glu Ile Lys Leu Ala Gln Asn Val Thr Gly Asn Ser Gly Ile Asn Leu
145                 150                 155                 160

Thr Cys Thr Ser Lys Gln Gly His Pro Lys Pro Lys Lys Met Tyr Phe
                165                 170                 175

Leu Ile Thr Asn Ser Thr Asn Glu Tyr Gly Asp Asn Met Gln Ile Ser
            180                 185                 190

Gln Asp Asn Val Thr Glu Leu Phe Ser Ile Ser Asn Ser Leu Ser Leu
            195                 200                 205

Ser Phe Pro Asp Gly Val Trp His Met Thr Val Val Cys Val Leu Glu
210                 215                 220

Thr Glu Ser Met Lys Ile Ser Ser Lys Pro Leu Asn Phe Thr Gln Glu
225                 230                 235                 240

Phe Pro Ser Pro Gln Thr Tyr Trp Lys Glu Ile Thr Ala Ser Val Thr
            245                 250                 255

Val Ala Leu Leu Leu Val Met Leu Leu Ile Ile Val Cys His Lys Lys
            260                 265                 270

Pro Asn Gln Pro Ser Arg Pro Ser Asn Thr Ala Ser Lys Leu Glu Arg
            275                 280                 285
```

```
Asp Ser Asn Ala Asp Arg Glu Thr Ile Asn Leu Lys Glu Leu Glu Pro
    290                 295                 300

Gln Ile Ala Ser Ala Lys Pro Asn Ala Glu
305                 310
```

<210> SEQ ID NO 15
<211> LENGTH: 303
<212> TYPE: PRT
<213> ORGANISM: Mus musculus

<400> SEQUENCE: 15

```
Met Gly Leu Ala Ile Leu Ile Phe Val Thr Val Leu Leu Ile Ser Asp
  1               5                  10                  15

Ala Val Ser Val Glu Thr Gln Ala Tyr Phe Asn Gly Thr Ala Tyr Leu
             20                  25                  30

Pro Cys Pro Phe Thr Lys Ala Gln Asn Ile Ser Leu Ser Glu Leu Val
         35                  40                  45

Val Phe Trp Gln Asp Gln Gln Lys Leu Val Leu Tyr Glu His Tyr Leu
 50                  55                  60

Gly Thr Glu Lys Leu Asp Ser Val Asn Ala Lys Tyr Leu Gly Arg Thr
 65                  70                  75                  80

Ser Phe Asp Arg Asn Asn Trp Thr Leu Arg Leu His Asn Val Gln Ile
                 85                  90                  95

Lys Asp Met Gly Ser Tyr Asp Cys Phe Ile Gln Lys Pro Pro Thr
            100                 105                 110

Gly Ser Ile Ile Leu Gln Gln Thr Leu Thr Glu Leu Ser Val Ile Ala
        115                 120                 125

Asn Phe Ser Glu Pro Glu Ile Lys Leu Ala Gln Asn Val Thr Gly Asn
    130                 135                 140

Ser Gly Ile Asn Leu Thr Cys Thr Ser Lys Gln Gly His Pro Lys Pro
145                 150                 155                 160

Lys Lys Met Tyr Phe Leu Ile Thr Asn Ser Thr Asn Glu Tyr Gly Asp
                165                 170                 175

Asn Met Gln Ile Ser Gln Asp Asn Val Thr Glu Leu Phe Ser Ile Ser
            180                 185                 190

Asn Ser Leu Ser Leu Ser Phe Pro Asp Gly Val Trp His Met Thr Val
        195                 200                 205

Val Cys Val Leu Glu Thr Glu Ser Met Lys Ile Ser Ser Lys Pro Leu
    210                 215                 220

Asn Phe Thr Gln Glu Phe Pro Ser Pro Gln Thr Tyr Trp Lys Glu Ile
225                 230                 235                 240

Thr Ala Ser Val Thr Val Ala Leu Leu Leu Val Met Leu Leu Ile Ile
                245                 250                 255

Val Cys His Lys Lys Pro Asn Gln Pro Ser Arg Pro Ser Asn Thr Ala
            260                 265                 270

Ser Lys Leu Glu Arg Asp Ser Asn Ala Asp Arg Glu Thr Ile Asn Leu
        275                 280                 285

Lys Glu Leu Glu Pro Gln Ile Ala Ser Ala Lys Pro Asn Ala Glu
    290                 295                 300
```

<210> SEQ ID NO 16
<211> LENGTH: 356
<212> TYPE: PRT
<213> ORGANISM: Mus musculus

<400> SEQUENCE: 16

```
Met Ala Lys Thr Ile Arg Arg Leu Ser Val Ala Phe Leu Thr Leu Ser
 1               5                  10                  15

Asp Arg Gly Pro His Tyr Lys Ile Leu Leu Pro Leu Pro His Lys Gly
            20                  25                  30

Trp Thr Pro Gly Leu Thr His Asn Ala Ser Leu Tyr Cys Ala Ser Ile
        35                  40                  45

Ile Leu Lys Asn Thr Met Gly Leu Ala Ile Leu Ile Phe Val Thr Val
     50                  55                  60

Leu Leu Ile Ser Asp Ala Val Ser Val Glu Thr Gln Ala Tyr Phe Asn
 65                  70                  75                  80

Gly Thr Ala Tyr Leu Pro Cys Pro Phe Thr Lys Ala Gln Asn Ile Ser
                85                  90                  95

Leu Ser Glu Leu Val Val Phe Trp Gln Asp Gln Gln Lys Leu Val Leu
            100                 105                 110

Tyr Glu His Tyr Leu Gly Thr Glu Lys Leu Asp Ser Val Asn Ala Lys
        115                 120                 125

Tyr Leu Gly Arg Thr Ser Phe Asp Arg Asn Asn Trp Thr Leu Arg Leu
    130                 135                 140

His Asn Val Gln Ile Lys Asp Met Gly Ser Tyr Asp Cys Phe Ile Gln
145                 150                 155                 160

Lys Lys Pro Pro Thr Gly Ser Ile Ile Leu Gln Gln Thr Leu Thr Glu
                165                 170                 175

Leu Ser Val Ile Ala Asn Phe Ser Glu Pro Glu Ile Lys Leu Ala Gln
            180                 185                 190

Asn Val Thr Gly Asn Ser Gly Ile Asn Leu Thr Cys Thr Ser Lys Gln
        195                 200                 205

Gly His Pro Lys Pro Lys Met Tyr Phe Leu Ile Thr Asn Ser Thr
    210                 215                 220

Asn Glu Tyr Gly Asp Asn Met Gln Ile Ser Gln Asp Asn Val Thr Glu
225                 230                 235                 240

Leu Phe Ser Ile Ser Asn Ser Leu Ser Leu Ser Phe Pro Asp Gly Val
                245                 250                 255

Trp His Met Thr Val Val Cys Val Leu Glu Thr Glu Ser Met Lys Ile
            260                 265                 270

Ser Ser Lys Pro Leu Asn Phe Thr Gln Glu Phe Pro Ser Pro Gln Thr
        275                 280                 285

Tyr Trp Lys Glu Ile Thr Ala Ser Val Thr Val Ala Leu Leu Leu Val
    290                 295                 300

Met Leu Leu Ile Ile Val Cys His Lys Lys Pro Asn Gln Pro Ser Arg
305                 310                 315                 320

Pro Ser Asn Thr Ala Ser Lys Leu Glu Arg Asp Ser Asn Ala Asp Arg
                325                 330                 335

Glu Thr Ile Asn Leu Lys Glu Leu Glu Pro Gln Ile Ala Ser Ala Lys
            340                 345                 350

Pro Asn Ala Glu
        355
```

<210> SEQ ID NO 17
<211> LENGTH: 356
<212> TYPE: PRT
<213> ORGANISM: Mus musculus

<400> SEQUENCE: 17

Met Ala Lys Thr Ile Arg Arg Leu Ser Val Ala Phe Leu Thr Leu Ser

```
                1               5                  10                  15
Asp Arg Gly Pro His Tyr Lys Ile Leu Leu Pro Leu Pro His Lys Gly
                   20                  25                  30

Trp Thr Pro Gly Leu Thr His Asn Ala Ser Leu Tyr Cys Ala Ser Ile
           35                  40                  45

Ile Leu Lys Asn Thr Met Gly Leu Ala Ile Leu Ile Phe Val Thr Val
       50                  55                  60

Leu Leu Ile Ser Asp Ala Val Ser Val Glu Thr Gln Ala Tyr Phe Asn
65                  70                  75                  80

Gly Thr Ala Tyr Leu Pro Cys Pro Phe Thr Lys Ala Gln Asn Ile Ser
               85                  90                  95

Leu Ser Glu Leu Val Val Phe Trp Gln Asp Gln Gln Lys Leu Val Leu
                   100                 105                 110

Tyr Glu His Tyr Leu Gly Thr Glu Lys Leu Asp Ser Val Asn Ala Lys
           115                 120                 125

Tyr Leu Gly Arg Thr Ser Phe Asp Arg Asn Asn Trp Thr Leu Arg Leu
       130                 135                 140

His Asn Val Gln Ile Lys Asp Met Gly Ser Tyr Asp Cys Phe Ile Gln
145                 150                 155                 160

Lys Lys Pro Pro Thr Gly Ser Ile Ile Leu Gln Gln Thr Leu Thr Glu
               165                 170                 175

Leu Ser Val Ile Ala Asn Phe Ser Glu Pro Glu Ile Lys Leu Ala Gln
                   180                 185                 190

Asn Val Thr Gly Asn Ser Gly Ile Asn Leu Thr Cys Thr Ser Lys Gln
           195                 200                 205

Gly His Pro Lys Pro Lys Lys Met Tyr Phe Leu Ile Thr Asn Ser Thr
       210                 215                 220

Asn Glu Tyr Gly Asp Asn Met Gln Ile Ser Gln Asp Asn Val Thr Glu
225                 230                 235                 240

Leu Phe Ser Ile Ser Asn Ser Leu Ser Leu Ser Phe Pro Asp Gly Val
               245                 250                 255

Trp His Met Thr Val Val Cys Val Leu Glu Thr Glu Ser Met Lys Ile
                   260                 265                 270

Ser Ser Lys Pro Leu Asn Phe Thr Gln Glu Phe Pro Ser Pro Gln Thr
           275                 280                 285

Tyr Trp Lys Glu Ile Thr Ala Ser Val Thr Val Ala Leu Leu Leu Val
       290                 295                 300

Met Leu Leu Ile Ile Val Cys His Lys Lys Pro Asn Gln Pro Ser Arg
305                 310                 315                 320

Pro Ser Asn Thr Ala Ser Lys Leu Glu Arg Asp Ser Asn Ala Asp Arg
               325                 330                 335

Glu Thr Ile Asn Leu Lys Glu Leu Glu Pro Gln Ile Ala Ser Ala Lys
                   340                 345                 350

Pro Asn Ala Glu
           355

<210> SEQ ID NO 18
<211> LENGTH: 309
<212> TYPE: PRT
<213> ORGANISM: Mus musculus

<400> SEQUENCE: 18

Met Asp Pro Arg Cys Thr Met Gly Leu Ala Ile Leu Ile Phe Val Thr
1               5                  10                  15
```

```
Val Leu Leu Ile Ser Asp Ala Val Ser Val Glu Thr Gln Ala Tyr Phe
             20                  25                  30

Asn Gly Thr Ala Tyr Leu Pro Cys Pro Phe Thr Lys Ala Gln Asn Ile
         35                  40                  45

Ser Leu Ser Glu Leu Val Val Phe Trp Gln Asp Gln Gln Lys Leu Val
 50                  55                  60

Leu Tyr Glu His Tyr Leu Gly Thr Glu Lys Leu Asp Ser Val Asn Ala
 65                  70                  75                  80

Lys Tyr Leu Gly Arg Thr Ser Phe Asp Arg Asn Asn Trp Thr Leu Arg
                 85                  90                  95

Leu His Asn Val Gln Ile Lys Asp Met Gly Ser Tyr Asp Cys Phe Ile
            100                 105                 110

Gln Lys Lys Pro Pro Thr Gly Ser Ile Ile Leu Gln Gln Thr Leu Thr
            115                 120                 125

Glu Leu Ser Val Ile Ala Asn Phe Ser Glu Pro Glu Ile Lys Leu Ala
130                 135                 140

Gln Asn Val Thr Gly Asn Ser Gly Ile Asn Leu Thr Cys Thr Ser Lys
145                 150                 155                 160

Gln Gly His Pro Lys Pro Lys Lys Met Tyr Phe Leu Ile Thr Asn Ser
                165                 170                 175

Thr Asn Glu Tyr Gly Asp Asn Met Gln Ile Ser Gln Asp Asn Val Thr
            180                 185                 190

Glu Leu Phe Ser Ile Ser Asn Ser Leu Ser Leu Ser Phe Pro Asp Gly
            195                 200                 205

Val Trp His Met Thr Val Val Cys Val Leu Glu Thr Glu Ser Met Lys
210                 215                 220

Ile Ser Ser Lys Pro Leu Asn Phe Thr Gln Glu Phe Pro Ser Pro Gln
225                 230                 235                 240

Thr Tyr Trp Lys Glu Ile Thr Ala Ser Val Thr Val Ala Leu Leu Leu
                245                 250                 255

Val Met Leu Leu Ile Ile Val Cys His Lys Lys Pro Asn Gln Pro Ser
            260                 265                 270

Arg Pro Ser Asn Thr Ala Ser Lys Leu Glu Arg Asp Ser Asn Ala Asp
            275                 280                 285

Arg Glu Thr Ile Asn Leu Lys Glu Leu Glu Pro Gln Ile Ala Ser Ala
290                 295                 300

Lys Pro Asn Ala Glu
305

<210> SEQ ID NO 19
<211> LENGTH: 314
<212> TYPE: PRT
<213> ORGANISM: Mus musculus

<400> SEQUENCE: 19

Met Tyr Val Ile Lys Thr Cys Ala Thr Cys Thr Met Gly Leu Ala Ile
 1               5                  10                  15

Leu Ile Phe Val Thr Val Leu Leu Ile Ser Asp Ala Val Ser Val Glu
             20                  25                  30

Thr Gln Ala Tyr Phe Asn Gly Thr Ala Tyr Leu Pro Cys Pro Phe Thr
         35                  40                  45

Lys Ala Gln Asn Ile Ser Leu Ser Glu Leu Val Val Phe Trp Gln Asp
 50                  55                  60

Gln Gln Lys Leu Val Leu Tyr Glu His Tyr Leu Gly Thr Glu Lys Leu
 65                  70                  75                  80
```

-continued

Asp Ser Val Asn Ala Lys Tyr Leu Gly Arg Thr Ser Phe Asp Arg Asn
                85                  90                  95

Asn Trp Thr Leu Arg Leu His Asn Val Gln Ile Lys Asp Met Gly Ser
            100                 105                 110

Tyr Asp Cys Phe Ile Gln Lys Lys Pro Pro Thr Gly Ser Ile Ile Leu
        115                 120                 125

Gln Gln Thr Leu Thr Glu Leu Ser Val Ile Ala Asn Phe Ser Glu Pro
    130                 135                 140

Glu Ile Lys Leu Ala Gln Asn Val Thr Gly Asn Ser Gly Ile Asn Leu
145                 150                 155                 160

Thr Cys Thr Ser Lys Gln Gly His Pro Lys Pro Lys Lys Met Tyr Phe
                165                 170                 175

Leu Ile Thr Asn Ser Thr Asn Glu Tyr Gly Asp Asn Met Gln Ile Ser
            180                 185                 190

Gln Asp Asn Val Thr Glu Leu Phe Ser Ile Ser Asn Ser Leu Ser Leu
        195                 200                 205

Ser Phe Pro Asp Gly Val Trp His Met Thr Val Val Cys Val Leu Glu
    210                 215                 220

Thr Glu Ser Met Lys Ile Ser Ser Lys Pro Leu Asn Phe Thr Gln Glu
225                 230                 235                 240

Phe Pro Ser Pro Gln Thr Tyr Trp Lys Glu Ile Thr Ala Ser Val Thr
                245                 250                 255

Val Ala Leu Leu Leu Val Met Leu Leu Ile Ile Val Cys His Lys Lys
            260                 265                 270

Pro Asn Gln Pro Ser Arg Pro Ser Asn Thr Ala Ser Lys Leu Glu Arg
        275                 280                 285

Asp Ser Asn Ala Asp Arg Glu Thr Ile Asn Leu Lys Glu Leu Glu Pro
    290                 295                 300

Gln Ile Ala Ser Ala Lys Pro Asn Ala Glu
305                 310

<210> SEQ ID NO 20
<211> LENGTH: 303
<212> TYPE: PRT
<213> ORGANISM: Mus musculus

<400> SEQUENCE: 20

Met Gly Leu Ala Ile Leu Ile Phe Val Thr Val Leu Leu Ile Ser Asp
 1               5                  10                  15

Ala Val Ser Val Glu Thr Gln Ala Tyr Phe Asn Gly Thr Ala Tyr Leu
            20                  25                  30

Pro Cys Pro Phe Thr Lys Ala Gln Asn Ile Ser Leu Ser Glu Leu Val
        35                  40                  45

Val Phe Trp Gln Asp Gln Gln Lys Leu Val Leu Tyr Glu His Tyr Leu
    50                  55                  60

Gly Thr Glu Lys Leu Asp Ser Val Asn Ala Lys Tyr Leu Gly Arg Thr
65                  70                  75                  80

Ser Phe Asp Arg Asn Asn Trp Thr Leu Arg Leu His Asn Val Gln Ile
                85                  90                  95

Lys Asp Met Gly Ser Tyr Asp Cys Phe Ile Gln Lys Lys Pro Pro Thr
            100                 105                 110

Gly Ser Ile Ile Leu Gln Gln Thr Leu Thr Glu Leu Ser Val Ile Ala
        115                 120                 125

Asn Phe Ser Glu Pro Glu Ile Lys Leu Ala Gln Asn Val Thr Gly Asn

```
                130               135                140
Ser Gly Ile Asn Leu Thr Cys Thr Ser Lys Gln Gly His Pro Lys Pro
145                 150                 155                 160
Lys Lys Met Tyr Phe Leu Ile Thr Asn Ser Thr Asn Glu Tyr Gly Asp
                165                 170                 175
Asn Met Gln Ile Ser Gln Asp Asn Val Thr Glu Leu Phe Ser Ile Ser
                180                 185                 190
Asn Ser Leu Ser Leu Ser Phe Pro Asp Gly Val Trp His Met Thr Val
            195                 200                 205
Val Cys Val Leu Glu Thr Glu Ser Met Lys Ile Ser Ser Lys Pro Leu
210                 215                 220
Asn Phe Thr Gln Glu Phe Pro Ser Pro Gln Thr Tyr Trp Lys Glu Ile
225                 230                 235                 240
Thr Ala Ser Val Thr Val Ala Leu Leu Leu Val Met Leu Leu Ile Ile
                245                 250                 255
Val Cys His Lys Lys Pro Asn Gln Pro Ser Arg Pro Ser Asn Thr Ala
            260                 265                 270
Ser Lys Leu Glu Arg Asp Ser Asn Ala Asp Arg Glu Thr Ile Asn Leu
        275                 280                 285
Lys Glu Leu Glu Pro Gln Ile Ala Ser Ala Lys Pro Asn Ala Glu
    290                 295                 300
```

<210> SEQ ID NO 21
<211> LENGTH: 1424
<212> TYPE: DNA
<213> ORGANISM: Homo sapiens

<400> SEQUENCE: 21

```
aggagcctta ggaggtacgg ggagctcgca aatactcctt ttggtttatt cttaccacct     60
tgcttctgtg ttccttggga atgctgctgt gcttatgcat ctggtctctt tttggagcta   120
cagtggacag gcatttgtga cagcactatg ggactgagta acattctctt gtgatggcc    180
ttcctgctct ctggtgctgc tcctctgaag attcaagctt atttcaatga gactgcagac   240
ctgccatgcc aatttgcaaa ctctcaaaac caaagcctga gtgagctagt agtattttgg   300
caggaccagg aaaacttggt tctgaatgag gtatacttag caaagagaa atttgacagt    360
gttcattcca gtatatgggg ccgcacaagt tttgattcgg acagttggac cctgagactt   420
cacaatcttc agatcaagga caagggcttg tatcaatgta tcatccatca caaaagccc    480
acaggaatga ttcgcatcca ccagatgaat tctgaactgt cagtgcttgc taacttcagt   540
caacctgaaa tagtaccaat ttctaatata acagaaaatg tgtacataaa tttgacctgc   600
tcatctatac acggttaccc agaacctaag aagatgagtg ttttgctaag aaccaagaat   660
tcaactatcg agtatgatgg tattatgcag aaatctcaag ataatgtcac agaactgtac   720
gacgttttcca tcagccttgtc tgtttcattc cctgatgtta cgagcaatat gaccatcttc   780
tgtattctgg aaactgacaa gacgcggctt tatcttcac ctttctctat agagcttgag     840
gaccctcagc ctcccccaga ccacattcct tggattacag ctgtacttcc aacagttatt   900
atatgtgtga tggttttctg tctaattcta tggaaatgga agaagaagaa gcggcctcgc   960
aactcttata aatgtggaac caacacaatg gagagggaag agagtgaaca gaccaagaaa  1020
agagaaaaaa tccatatacc tgaaagatct gatgaagccc agcgtgtttt taaaagttcg  1080
aagacatctt catgcgacaa aagtgataca tgttttttaat taaagagtaa agcccataca  1140
agtattcatt ttttctaccc tttcctttgt aagttcctgg gcaaccttttt tgatttcttc  1200
```

-continued

```
cagaaggcaa aaagacatta ccatgagtaa taagggggct ccaggactcc ctctaagtgg   1260
aatagcctcc ctgtaactcc agctctgctc cgtatgccaa gaggagactt taattctctt   1320
actgcttctt ttcacttcag agcacactta tgggccaagc ccagcttaat ggctcatgac   1380
ctggaaataa aatttaggac caataaaaaa aaaaaaaaaa aaaa                    1424
```

<210> SEQ ID NO 22
<211> LENGTH: 323
<212> TYPE: PRT
<213> ORGANISM: Homo sapiens

<400> SEQUENCE: 22

```
Met Gly Leu Ser Asn Ile Leu Phe Val Met Ala Phe Leu Leu Ser Gly
 1               5                  10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
    130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
    210                 215                 220

Pro Phe Ser Ile Glu Leu Glu Asp Pro Gln Pro Pro Pro Asp His Ile
225                 230                 235                 240

Pro Trp Ile Thr Ala Val Leu Pro Thr Val Ile Ile Cys Val Met Val
                245                 250                 255

Phe Cys Leu Ile Leu Trp Lys Trp Lys Lys Lys Arg Pro Arg Asn
            260                 265                 270

Ser Tyr Lys Cys Gly Thr Asn Thr Met Glu Arg Glu Glu Ser Glu Gln
        275                 280                 285

Thr Lys Lys Arg Glu Lys Ile His Ile Pro Glu Arg Ser Asp Glu Ala
    290                 295                 300

Gln Arg Val Phe Lys Ser Ser Lys Thr Ser Ser Cys Asp Lys Ser Asp
305                 310                 315                 320

Thr Cys Phe
```

<210> SEQ ID NO 23
<211> LENGTH: 1183
<212> TYPE: DNA
<213> ORGANISM: Mus musculus

<400> SEQUENCE: 23

```
ggagcaagca gacgcgtaag agtggctcct gtaggcagca cggacttgaa caaccagact    60
cctgtagacg tgttccagaa cttacggaag cacccacgat ggaccccaga tgcaccatgg   120
gcttggcaat ccttatcttt gtgacagtct tgctgatctc agatgctgtt ccgtggaga    180
cgcaagctta tttcaatggg actgcatatc tgccgtgccc atttacaaag gctcaaaaca   240
taagcctgag tgagctggta gtattttggc aggaccagca aaagttggtt ctgtacgagc   300
actatttggg cacagagaaa cttgatagtg tgaatgccaa gtacctgggc cgcacgagct   360
ttgacaggaa caactggact ctacgacttc acaatgttca gatcaaggac atgggctcgt   420
atgattgttt tatacaaaaa aagccaccca caggatcaat tatcctccaa cagacattaa   480
cagaactgtc agtgatcgcc aacttcagtg aacctgaaat aaaactggct cagaatgtaa   540
caggaaattc tggcataaat ttgacctgca cgtctaagca aggtcacccg aaacctaaga   600
agatgtattt tctgataact aattcaacta atgagtatgg tgataacatg cagatatcac   660
aagataatgt cacagaactg ttcagtatct ccaacagcct ctctctttca ttcccggatg   720
gtgtgtggca tatgaccgtt gtgtgtgttc tggaaacgga gtcaatgaag atttcctcca   780
aacctctcaa tttcactcaa gagtttccat ctcctcaaac gtattggaag agattacag   840
cttcagttac tgtggccctc ctccttgtga tgctgctcat cattgtatgt cacaagaagc   900
cgaatcagcc tagcaggccc agcaacacag cctctaagtt agagcgggat agtaacgctg   960
acagagagac tatcaacctg aaggaacttg aaccccaaat tgcttcagca aaaccaaatg  1020
cagagtgaag gcagtgagag cctgaggaaa gagttaaaaa ttgctttgcc tgaaataaga  1080
agtgcagagt ttctcagaat tcaaaaatgt tctcagctga ttggaattct acagttgaat  1140
aattaaagaa caaatacac aacagtgaaa aaaaaaaaaa aaa                     1183
```

<210> SEQ ID NO 24
<211> LENGTH: 309
<212> TYPE: PRT
<213> ORGANISM: Mus musculus

<400> SEQUENCE: 24

```
Met Asp Pro Arg Cys Thr Met Gly Leu Ala Ile Leu Ile Phe Val Thr
 1               5                  10                  15

Val Leu Leu Ile Ser Asp Ala Val Ser Val Glu Thr Gln Ala Tyr Phe
            20                  25                  30

Asn Gly Thr Ala Tyr Leu Pro Cys Pro Phe Thr Lys Ala Gln Asn Ile
        35                  40                  45

Ser Leu Ser Glu Leu Val Val Phe Trp Gln Asp Gln Gln Lys Leu Val
    50                  55                  60

Leu Tyr Glu His Tyr Leu Gly Thr Glu Lys Leu Asp Ser Val Asn Ala
65                  70                  75                  80

Lys Tyr Leu Gly Arg Thr Ser Phe Asp Arg Asn Asn Trp Thr Leu Arg
                85                  90                  95

Leu His Asn Val Gln Ile Lys Asp Met Gly Ser Tyr Asp Cys Phe Ile
            100                 105                 110

Gln Lys Lys Pro Pro Thr Gly Ser Ile Ile Leu Gln Gln Thr Leu Thr
        115                 120                 125
```

```
Glu Leu Ser Val Ile Ala Asn Phe Ser Glu Pro Glu Ile Lys Leu Ala
    130                 135                 140

Gln Asn Val Thr Gly Asn Ser Gly Ile Asn Leu Thr Cys Thr Ser Lys
145                 150                 155                 160

Gln Gly His Pro Lys Pro Lys Lys Met Tyr Phe Leu Ile Thr Asn Ser
                165                 170                 175

Thr Asn Glu Tyr Gly Asp Asn Met Gln Ile Ser Gln Asp Asn Val Thr
            180                 185                 190

Glu Leu Phe Ser Ile Ser Asn Ser Leu Ser Leu Ser Phe Pro Asp Gly
        195                 200                 205

Val Trp His Met Thr Val Val Cys Val Leu Glu Thr Glu Ser Met Lys
    210                 215                 220

Ile Ser Ser Lys Pro Leu Asn Phe Thr Gln Glu Phe Pro Ser Pro Gln
225                 230                 235                 240

Thr Tyr Trp Lys Glu Ile Thr Ala Ser Val Thr Val Ala Leu Leu Leu
                245                 250                 255

Val Met Leu Leu Ile Ile Val Cys His Lys Lys Pro Asn Gln Pro Ser
            260                 265                 270

Arg Pro Ser Asn Thr Ala Ser Lys Leu Glu Arg Asp Ser Asn Ala Asp
        275                 280                 285

Arg Glu Thr Ile Asn Leu Lys Glu Leu Glu Pro Gln Ile Ala Ser Ala
    290                 295                 300

Lys Pro Asn Ala Glu
305

<210> SEQ ID NO 25
<211> LENGTH: 1112
<212> TYPE: DNA
<213> ORGANISM: Homo sapiens

<400> SEQUENCE: 25
cacagggtga aagctttgct tctctgctgc tgtaacaggg actagcacag acacacggat      60
gagtggggtc atttccagat attaggtcac agcagaagca gccaaaatgg atccccagtg     120
cactatggga ctgagtaaca ttctctttgt gatggccttc ctgctctctg gtgctgctcc     180
tctgaagatt caagcttatt tcaatgagac tgcagacctg ccatgccaat ttgcaaactc     240
tcaaaaccaa agcctgagtg agctagtagt attttggcag gaccaggaaa acttggttct     300
gaatgaggta tacttaggca agagaaattt gacagtgtt cattccaagt atatgggccg     360
cacaagtttt gattcggaca gttggaccct gagacttcac aatcttcaga tcaaggacaa     420
gggcttgtat caatgtatca tccatcacaa aaagcccaca ggaatgattc gcatccacca     480
gatgaattct gaactgtcag tgcttgctaa cttcagtcaa cctgaaatag taccaatttc     540
taatataaca gaaaatgtgt acataaattt gacctgctca tctatacacg gttacccaga     600
acctaagaag atgagtgttt tgctaagaac caagaattca actatcgagt atgatggtat     660
tatgcagaaa tctcaagata atgtcacaga actgtacgac gtttccatca gcttgtctgt     720
ttcattccct gatgttacga gcaatatgac catcttctgt attctggaaa ctgacaagac     780
gcggctttta tcttcacctt tctctataga gcttgaggac cctcagcctc ccccagacca     840
cattccttgg attacagctg tacttccaac agttattata tgtgtgatgg ttttctgtct     900
aattctatgg aaatggaaga agaagaagcg ccctcgcaac tctttataaat gtggaaccaa     960 cacaatggag agggaagaga gtgaacagac caagaaaaga gaaaaaatcc atatacctga    1020
```

```
aagatctgat gaagcccagc gtgttttta  aagttcgaag acatcttcat gcgacaaaag    1080
tgatacatgt ttttaattaa agagtaaagc cc                                  1112
```

<210> SEQ ID NO 26
<211> LENGTH: 329
<212> TYPE: PRT
<213> ORGANISM: Homo sapiens

<400> SEQUENCE: 26

```
Met Asp Pro Gln Cys Thr Met Gly Leu Ser Asn Ile Leu Phe Val Met
 1               5                  10                  15

Ala Phe Leu Leu Ser Gly Ala Ala Pro Leu Lys Ile Gln Ala Tyr Phe
             20                  25                  30

Asn Glu Thr Ala Asp Leu Pro Cys Gln Phe Ala Asn Ser Gln Asn Gln
         35                  40                  45

Ser Leu Ser Glu Leu Val Val Phe Trp Gln Asp Gln Glu Asn Leu Val
     50                  55                  60

Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                 85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325
```

SURFACE RECEPTOR ANTIGEN VACCINES

CROSS-REFERENCE TO RELATED APPLICATION

This application is a continuation of U.S. patent application Ser. No. 09/441,411, filed Nov. 16, 1999, which claims the benefit of U.S. Provisional Patent Application No. 60/109,106, filed Nov. 18, 1998, which are incorporated herein by reference in their entireties.

TECHNICAL FIELD

The invention relates to DNA vaccines, or vaccines containing molecules encoded by such DNA, for the induction of specific, sustained high titer antibody responses. More specifically, the invention is directed to DNA vaccines that comprise recombinant expression constructs encoding a cell surface receptor antigen and one or more immune response altering molecules.

BACKGROUND OF THE INVENTION

It is known in the immunological arts to provide certain vaccines according to a variety of formulations, usually for the purpose of inducing a desired immune response in a host. The immune system has been characterized as distinguishing foreign agents (or "non-self") agents from familiar or "self" components, such that foreign agents elicit immune responses while "self" components are ignored or tolerated. Immune responses have traditionally been characterized as either humoral responses, in which antibodies specific for antigens are produced by differentiated B lymphocytes known as plasma cells, or cell mediated responses, in which various types of T lymphocytes act to eliminate antigens by a number of mechanisms. For example, CD4+ helper T cells that are capable of recognizing specific antigens may respond by releasing soluble mediators such as cytokines to recruit additional cells of the immune system to participate in an immune response. Also, CD8+ cytotoxic T cells that are also capable of specific antigen recognition may respond by binding to and destroying or damaging an antigen-bearing cell or particle.

Several strategies for eliciting specific immune responses through the administration of a vaccine to a host include immunization with heat-killed or with live, attenuated infectious pathogens such as viruses, bacteria or certain eukaryotic pathogens; immunization with a non-virulent infective agent capable of directing the expression of genetic material encoding the antigen(s) to which an immune response is desired; and immunization with subunit vaccines that contain isolated immunogens (such as proteins) from a particular pathogen in order to induce immunity against the pathogen. (See, e.g., Liu, 1998 *Nature Medicine* 4(5 suppl.):515.) Each of these approaches is compromised by certain trade-offs between safety and efficacy. Moreover, there may be certain types of desirable immunity for which none of these approaches has been particularly effective, including the development of vaccines that are effective in protecting a host immunologically against cancer, autoimmune disease, human immunodeficiency viruses or other clinical conditions.

In a number of contexts, it may be desirable to induce an immune response in a host that involves specific immune recognition of a cell surface receptor antigen (SRA). Such a target structure may be, for example, a host molecule, an altered (e.g., mutated, degraded, incompletely synthesized, conformationally changed, etc.) or inappropriately expressed host molecule or a foreign molecule. For example, numerous cell SRA have been implicated in cancer as unique or preferentially expressed markers of tumor cells, such that targeting an immune response to such SRA appears to be a useful strategy, albeit an approach still in need of refinement. (See, e.g., Pardoll, 1998 *Nature Medicine* 4(5 supp):525 and references cited therein.) In particular, many such approaches may provide induction of only weak or transient host immune responses, or of responses where induction of cell mediated and/or humoral immune response components is ineffective. Recent interest in therapeutic passive immunity conferred by the administration of SRA-specific monoclonal antibodies underscores the significance of SRA (see, e.g., Pietras et al., 1994 *Oncogene* 9:1829; Baselga et al, 1998 *Canc. Res.* 58:2825; Hoffinann et al., 1997 *Anticanc. Res.* 17:4419; Bier et al., 1998 *Canc. Immunol. Immunother.* 46:167; Petit et al., 1997 *Am. J. Pathol.* 151:1523; Udayachander et al., 1997 *Hum. Antibod.* 8:60.) but does not offer the longer-lived protection afforded by a vaccine, which influences the host immune state.

Clearly there is a need for improved vaccines, and in particular for vaccines that are directed to inducing immune responses specific for cell surface receptor antigens. The present invention provides compositions and methods for cell surface receptor antigen specific vaccines, and other related advantages.

SUMMARY OF THE INVENTION

The invention provides compositions and methods for altering an immune response in a host in an antigen specific manner, wherein the antigen is a cell surface receptor antigen. Vaccines are provided that include a gene encoding a desired cell surface antigen receptor (or the expressed product) and one or more genes encoding immune response altering molecules (or the expressed products).

In one aspect, the invention is directed to a vaccine for eliciting or enhancing the titer of antibodies specific for a cell surface receptor antigen, comprising a recombinant expression construct comprising at least one promoter operably linked to a nucleic acid sequence encoding a cell surface receptor antigen, a nucleic acid sequence encoding a first immune response altering molecule and a nucleic acid sequence encoding a second immune response altering molecule, wherein the first and second immune response altering molecules are different from each other and are an accessory cell agent and a T cell agent. In one embodiment, the vaccine for eliciting or enhancing the titer of antibodies specific for a cell surface receptor antigen comprises the expression products of such a recombinant expression construct.

In another embodiment the invention provides a vaccine for eliciting or enhancing the titer of antibodies specific for a cell surface receptor antigen, comprising a first recombinant expression construct containing at least one promoter operably linked to a nucleic acid sequence encoding a cell surface receptor antigen and a nucleic acid sequence encoding a first immune response altering molecule; and a second recombinant expression construct containing a promoter operably linked to a nucleic acid sequence encoding a second immune response altering molecule, wherein the first and second immune response altering molecules are different from each other and are an accessory cell agent and a T cell agent. In a further embodiment, the vaccine for eliciting or enhancing the titer of antibodies specific for a cell surface receptor antigen comprises the expression products of such recombinant expression constructs.

In another embodiment the invention provides a vaccine for eliciting or enhancing the titer of antibodies specific for a cell surface receptor antigen, comprising a first recombinant expression construct containing at least one promoter operably linked to a nucleic acid sequence encoding a cell surface receptor antigen; a second recombinant expression construct containing a promoter operably linked to a nucleic acid sequence encoding a first immune response altering molecule; and a third recombinant expression construct containing a promoter operably linked to a nucleic acid sequence encoding a second immune response altering molecule, wherein the first and second immune response altering molecules are different from each other and are an accessory cell agent and a T cell agent. In a further embodiment, the vaccine for eliciting or enhancing the titer of antibodies specific for a cell surface receptor antigen comprises the expression products of such recombinant expression constructs.

In yet another embodiment, the invention provides a vaccine for eliciting or enhancing the titer of antibodies specific for a cell surface receptor antigen, comprising a first recombinant expression construct containing at least one promoter operably linked to a nucleic acid sequence encoding a cell surface receptor antigen; and a second recombinant expression construct containing at least one promoter operably linked to a nucleic acid sequence encoding a first immune response altering molecule and a nucleic acid sequence encoding a second immune response altering molecule, wherein the first and second immune response altering molecules are different from each other and are an accessory cell agent and a T cell agent. In a further embodiment, the vaccine for eliciting or enhancing the titer of antibodies specific for a cell surface receptor antigen comprises the expression products of such recombinant expression constructs.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE DRAWINGS

FIG. 1 illustrates enzyme linked immunosorbent assay results showing induction of SRA specific antibodies by immunization in an animal model system with DNA vaccines containing SRA and IRAM encoding nucleic acid sequences.

FIG. 2 shows the T:B lymphocyte ratios in mice immunized with DNA vaccines containing SRA and/or IRAM encoding nucleic acid sequences as detected by immunocytofluorimetry.

FIG. 3 depicts results obtained in an animal model system wherein tumor growth is monitored following tumor challenge in hosts immunized with DNA vaccines containing SRA and IRAM encoding nucleic acid sequences.

DETAILED DESCRIPTION OF THE INVENTION

The present invention is directed to nucleic acid-based vaccines for altering the magnitude, duration and quality of immune responses directed against specific cell surface receptor antigens (referred to herein as "SRA"). More specifically, the invention relates to DNA vaccines comprising nucleic acids encoding SRA and nucleic acids encoding one or more immune response altering molecules (referred to herein as "IRAM"). The invention also relates to vaccines containing expressed SRA and IRAM products. As provided herein, the vaccines of the subject invention possess the unexpected property of eliciting sustained high titers of antibodies specific for a SRA.

The invention thus provides compositions for altering immune responses in a host capable of mounting an immune response. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Immune responses may often be regarded, for instance, as discrimination between self and non-self structures by the cells and tissues of a host's immune system at the molecular and cellular levels, but the invention should not be so limited. For example, immune responses may also include immune system state changes that result from immune recognition of self molecules, cells or tissues, as may accompany any number of normal conditions such as typical regulation of immune system components, or as may be present in pathological conditions such as the inappropriate autoimmune responses observed in autoimmune and degenerative diseases. As another example, in addition to induction by up-regulation of particular immune system activities (such as antibody and/or cytokine production, or activation of cell mediated immunity) immune responses may also include suppression, attenuation or any other down-regulation of detectable immunity, which may be the consequence of the antigen selected, the route of antigen administration, specific tolerance induction or other factors.

In particularly preferred embodiments of the present invention, the vaccine compositions and methods provided herein offer the surprising advantage of inducing high and sustained titers of SRA specific antibodies in a host that would otherwise be incapable of, or capable only of mounting a far weaker, humoral (i.e., antibody) response specific for the SRA. Those having ordinary skill in the art will appreciate, with respect to these embodiments, that sustained high antibody titers in a host represent maturation of an immune response and selection within the immune system of plasma cells that have differentiated from clonally expanded B lymphocyte subpopulations expressing immunoglobulin variable (V) regions having high affinity for an eliciting antigen. Such persons will further appreciate that such a maturation of the immune response is often accompanied by the production of antibodies that are predominantly of the IgG isotype, which may offer certain advantages related to structural and/or functional attributes of the immunoglobulin gamma heavy chain.

According to the present invention, SRA vaccines are provided that, in one embodiment, are DNA vaccines comprising one or more recombinant expression constructs encoding at least one SRA and at least one IRAM. Thus, the present invention provides nucleic acid-based vaccines wherein the nucleic acid may be in the form of RNA or DNA, including cDNA, genomic DNA and synthetic DNA as described below, such that references herein to "DNA vaccines" and the like are not intended to exclude these other forms in which the nucleic acid may be present. In particularly preferred embodiments, the SRA vaccine comprises at least one recombinant expression construct encoding an SRA and at least two IRAM, where at least one IRAM is a T cell agent and at least one IRAM is an accessory cell agent. In other preferred embodiments, the SRA vaccine comprises at least one recombinant expression construct encoding an SRA and at least one IRAM that may be either a T cell agent or an accessory cell agent. As provided herein, according to the various aspects of the invention the SRA vaccine may comprise a single recombinant expression construct that includes nucleic acid sequences encoding an SRA and one IRAM, two IRAM or a plurality (i.e., greater than two) of IRAM.

In other embodiments of the invention, the SRA vaccine may comprise a first and a second recombinant expression construct, wherein the first construct includes nucleic acid sequences encoding an SRA and at least one IRAM and the second construct includes nucleic acid sequences encoding at least one IRAM. In preferred embodiments, at least one encoded IRAM is a T cell agent and at least one encoded IRAM is an accessory cell agent such that the T cell agent and the accessory cell agent are encoded on different constructs. In other embodiments of the invention, the SRA vaccine may comprise at least three recombinant expression constructs wherein at least one construct includes nucleic acid sequences that encode a SRA, at least one construct includes nucleic acids that encode an IRAM that is a T cell agent, and at least one construct includes nucleic acids that encode an IRAM that is an accessory cell agent. In another particularly preferred embodiment, the SRA vaccine may comprise a first and a second recombinant expression construct, wherein the first construct includes nucleic acid sequences encoding a SRA and the second construct includes nucleic acid sequences encoding at least a first and optionally a second IRAM. This embodiment further permits simple preparation of vaccines that elicit or enhance the titer of antibodies specific for any of a number of different SRA by interchanging any of a variety of SRA-encoding first constructs for administration with the second construct. These and related variations of the vaccines according to the instant disclosure are within the scope of the invention.

As noted above, the DNA vaccines of the present invention alter the magnitude (e.g., amount of antibody produced), duration and/or quality (e.g., affinity of antibody produced for SRA) of immune responses directed at specific SRA. Surface receptor antigens (SRA) as used herein refers to any cell surface molecule against which an immune response is sought. Such antigens may be cell surface molecules that are stable or transient plasma membrane components, including peripheral, extrinsic, secretory, integral or transmembrane molecules, as long as any portion of the SRA is exposed at the exterior aspect of the plasma membrane of the cell in which the SRA occurs. In particularly preferred embodiments, the SRA is a cell surface molecule of known structure and having a known or described function, including but not limited to SRA having any of the receptor activities described in references cited for the following cell surface receptors: HER1 (e.g., GenBank Accession Nos. U48722, SEG_HEGFREXS, KO3193), HER2 (Yoshino et al., 1994 *J. Immunol.* 152:2393; Disis et al., 1994 *Canc. Res.* 54:16; see also, e.g., GenBank Acc. Nos. X03363 (SEQ ID NOS: 5-6), M17730 (SEQ ID NOS: 7-8), SEG_HUMHER20 (SEQ ID NO: 9)), HER3 (e.g., GenBank Acc. Nos. U29339, M34309), HER4 (Plowman et al., 1993 *Nature* 366:473; see also e.g., GenBank Acc. Nos. L07868, T64105), epidermal growth factor receptor (EGFR) (e.g., GenBank Acc. Nos. U48722 SEG_HEGFREXS, KO3193), vascular endothelial cell growth factor(e.g., GenBank No. M32977), vascular endothelial cell growth factor receptor (e.g., GenBank Acc. Nos. AF022375, 1680143, U48801, X62568), insulin-like growth factor-I (e.g., GenBank Acc. Nos. X00173, X56774, X56773, X06043, see also European Patent No. GB 2241703), insulin-like growth factor-II (e.g., GenBank Acc. Nos. X03562, X00910, SEG_HUMGFIA, SEG_HUMGFI2, M17863, M17862), transferrin receptor (Trowbridge and Omary, 1981 *Proc. Nat. Acad. USA* 78:3039; see also e.g., GenBank Acc. Nos. X01060, M11507), estrogen receptor (e.g., GenBank Acc. Nos. M38651, X03635, X99101, U47678, M12674), progesterone receptor (e.g., GenBank Acc. Nos. X51730, X69068, M15716), follicle stimulating hormone receptor (FSH-R) (e.g., GenBank Acc. Nos. Z34260, M65085), retinoic acid receptor (e.g., GenBank Acc. Nos. L12060, M60909, X77664, X57280, X07282, X06538), MUC-1 (Barnes et al., 1989 *Proc. Nat. Acad Sci. USA* 86:7159; see also e.g., GenBank Acc. Nos. SEG_MUSMUCIO, M65132, M64928) NY-ESO-1 (e.g., GenBank Acc. Nos. AJ003149, U87459), NA 17-A (e.g., European Patent No. WO 96/40039), Melan-A/MART-1 (Kawakami et al., 1994 *Proc. Nat. Acad Sci. USA* 91:3515; see also e.g., GenBank Acc. Nos. U06654, U06452), tyrosinase (Topalian et al., 1994 *Proc. Nat. Acad Sci. USA* 91:9461; see also e.g., GenBank Acc. Nos. M26729, SEG_HUMTYRO, see also Weber et al., *J. Clin. Invest* (1998) 102:1258), Gp-100 (Kawakami et al., 1994 *Proc. Nat. Acad Sci. USA* 91:3515; see also e.g., GenBank Acc. No. 573003, see also European Patent No. EP 668350; Adema et al., 1994 *J. Biol. Chem.* 269:20126), MAGE (van den Bruggen et al., 1991 *Science* 254:1643; see also e.g, GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735, M77481), BAGE (e.g., GenBank Acc. No. U19180, see also U.S. Pat. Nos. 5,683,886 and 5,571,711), GAGE (e.g., GenBank Acc. Nos. AF055475, AF055474, AF055473, U19147, U19146, U19145, U19144, U19143, U19142), any of the CTA class of receptors including in particular HOM-MEL-40 antigen encoded by the SSX2 gene (e.g., GenBank Acc. Nos. X86175, U90842, U90841, X86174), carcinoembyonic antigen (CEA, Gold and Freedman, 1985 *J Exp. Med* 121:439; see also e.g., GenBank Acc. Nos. SEG_HUMCEA, M59710, M59255, M29540), and PyLT (e.g., GenBank Acc. Nos. J02289, J02038).

In other highly preferred embodiments the SRA is a protein, glycoprotein or peptide (including a polypeptide) capable of being expressed by a host cell such that it localizes to the cell surface. SRA that localize to the cell surface may do so by virtue of having naturally present or artificially introduced structural features that direct the SRA to the cell surface, including by way of illustration and not limitation, secretory signal sequences, leader sequences, hydrophobic transmembrane domains, cell surface receptor binding domains, extracellular matrix binding domains, or any other structural feature that causes the SRA to localize to the cell surface. Such features are well known to those of ordinary skill in the art, who will further be familiar with methods for introducing nucleic acid sequences encoding these features into the subject expression constructs by genetic engineering, and with routine testing of such constructs to verify cell surface localization of the product. SRA may be the products of genes endogenous to the host in which the vaccine is administered, or of heterologous genes, or of modified homologous or heterologous genes including genes encoding mutated or chimeric products (e.g., fusion proteins) constructed using recombinant DNA methodologies, as known in the art and provided herein. Other SRA that are within the scope of the invention include SRA that are not proteins, glycoproteins or polypeptides, but that are structures the cell surface appearance of which may be directed by a suitable recombinant expression construct. For example, expression of defined carbohydrate cell surface antigens such as those present on specific glycolipids, glycoproteins, proteoglycans or the like, may be directed by one or more known enzyme(s) (e.g., glycosyltransferases) such that a vaccine according to the invention may comprise a recombinant expression construct comprising a nucleic acid sequence encoding such an enzyme.

As also noted above, the DNA vaccines of the present invention, which alter the magnitude, duration and quality of immune responses directed at specific SRA, further comprise at least one nucleic acid sequence encoding an immune response altering molecule (IRAM) IRAM as used herein includes any molecule that is, or that is capable of functioning as, an immune system component the occurrence of which may be influenced either by modifying expression levels within cells and/or tissues known to express the component and/or by changing the expression patterns (e.g., cell type, tissue type, lymphocyte subpopulation) of the component such that the quality or quantity of a SRA specific immune response is altered. As described above, certain preferred embodiments of the present invention contemplate a vaccine for eliciting sustained high titers of antibodies specific for a cell SRA comprising at least one recombinant expression construct encoding an SRA, at least one IRAM that is a T cell agent and at least one IRAM that is an accessory cell agent. In certain other preferred embodiments the vaccine may comprise at least one recombinant expression construct encoding an SRA and one IRAM that may be either a T cell agent or an accessory cell agent.

In certain highly preferred embodiments the IRAM is a protein, glycoprotein, peptide or polypeptide capable of being expressed by a host cell such that it localizes to the cell surface. IRAM that localize to the cell surface may do so by virtue of having naturally present or artificially introduced structural features that direct the IRAM to the cell surface, including by way of illustration and not limitation, secretory signal sequences, leader sequences, hydrophobic transmembrane domains, cell surface receptor binding domains, extracellular matrix binding domains, or any other structural feature that causes the IRAM to localize to the cell surface. Such features are well known to those of ordinary skill in the art, who will further be familiar with methods for introducing nucleic acid sequences encoding these features into the subject expression constructs by genetic engineering, and with routine testing of such constructs to verify cell surface localization of the product. IRAM may be the products of genes endogenous to the host in which the vaccine is administered, or of heterologous genes, or of modified homologous or heterologous genes including genes encoding mutated or chimeric products (e.g., fusion proteins) constructed using recombinant DNA methodologies, as known in the art and provided herein. Other IRAM that are within the scope of the invention include IRAM that are not proteins, glycoproteins or polypeptides, but that are structures the cell surface appearance of which may be directed by a suitable recombinant expression construct. For example, expression of defined carbohydrate cell surface antigens such as those present on specific glycolipids, glycoproteins, proteoglycans or the like, may be directed by one or more known enzyme(s) (e.g., glycosyltransferases) such that a vaccine according to the invention may comprise a recombinant expression construct comprising a nucleic acid sequence encoding such an enzyme.

In certain other preferred embodiments, the IRAM may be a soluble product that alters immune responses. Such soluble IRAM may be naturally occurring or artificially engineered variants of the cell surface IRAM described above, including isoforms of naturally occurring cell surface IRAM polypeptides that lack transmembrane domains or that contain processing sites such as protease cleavage sites that permit their liberation from cell surfaces. In other embodiments, soluble IRAM may include naturally occurring or artificially engineered variants (including, e.g., recombinant fusion proteins as provided herein) that typically are produced as soluble secreted or released products. Examples of such soluble IRAM include but need not be limited to cytokines, lymphokines, chemokines, motility factors, growth factors, hematopoietic factors, chemotactic factors, hormones, peptides and the like. Other soluble IRAM that are within the scope of the invention include IRAM that are not proteins, glycoproteins or polypeptides, but that are soluble mediators the appearance of which may be directed by a suitable recombinant expression construct. For example, expression of defined lipid mediators such as those derived from arachidonic acid, or other mediators, may be directed by one or more known enzyme(s) (e.g., cyclooxygenases such as COX1 and COX2, 5'-lipoxygenase) such that a vaccine according to the invention may comprise a recombinant expression construct comprising a nucleic acid sequence encoding such an enzyme.

As provided herein, an IRAM that is a T cell agent refers to a molecule typically produced by T cells, including but not limited to T cell surface molecules, secreted T cell soluble products or intracellular T cell components, that participates in any molecular or cellular event leading to a host immune response. These immune functions may include, for example, intermolecular recognition and/or binding events; immune cell/immunocyte induction and/or activation; immune cell-cell or molecule-cell interactions such as cell stimulation, intercellular signaling, transmembrane or intracellular signal transduction; initiation of specific transcriptional or translational activity; initiation of specific metabolic, catabolic, respiratory, cytoskeletal or motility, mitotic or apoptotic behavior; or any other molecular or cellular event associated with the generation of a host immune response. According to the present invention, an IRAM that is a T cell agent need not naturally be expressed exclusively by T cells. Additionally, according to the present invention an IRAM that is a T cell agent encoded by a recombinant expression construct of the subject vaccine need not be expressed exclusively by T cells of the host immunized using the subject vaccine, regardless of whether or not the T cell agent is ordinarily a gene product expressed uniquely in T cells, so long as the T cell agent encoded by the nucleic acid delivered in the vaccine provided has the effect of qualitatively or quantitatively altering a cell SRA specific immune response.

In particularly preferred embodiments, the T cell agent is a T cell surface molecule of known structure and having a known or described function, including but not limited to T cell agents having any of the T cell activation, adhesion, receptor/recognition, enzymatic or other activities described in references cited for the following cell surface receptors: CD2 (e.g., GenBank Acc. Nos. Y00023, SEG_HUMCD2, M16336, M16445, SEG_MUSCD2, M14362), 4-1BB (CDw137, Kwon et al., 1989 *Proc. Nat. Acad. Sci. USA*

86:1963, 4-1BB ligand (Goodwin et al., 1993 *Eur. J. Immunol.* 23:2361; Melero et al., 1998 *Eur. J. Immunol.* 3:116), CD5 (e.g., GenBank Acc. Nos. X78985, X89405), CD10 (e.g., GenBank Acc. Nos. M81591, X76732) CD27 (e.g., GenBank Acc. Nos. M63928, L24495, L08096), CD28 (June et al., 1990 Immunol. Today 11:211; see also, e.g., GenBank Acc. Nos. J02988, SEG_HUMCD28, M34563), CTLA4 (e.g., GenBank Acc. Nos. L15006, X05719, SEG_HUMIGCTL), CD40 (e.g., GenBank Acc. Nos. M83312, SEG_MUSC040A0, Y10507, X67878, X96710, U15637, L07414), interferon-γ (IFN-γ; see, e.g., Farrar et al. 1993 *Ann. Rev. Immunol.* 11:571 and references cited therein, Gray et al. 1982 *Nature* 295:503, Rinderknecht et al. 1984 *J. Biol. Chem.* 259:6790, DeGrado et al. 1982 *Nature* 300:379), interleukin4 (IL-4; see, e.g., 53$^{rd}$ *Forum in Immunology,* 1993 *Research in Immunol.* 144:553-643; Banchereau et al., 1994 in *The Cytokine Handbook,* 2$^{nd}$ ed., A. Thomson, ed., Academic Press, NY, p. 99; Keegan et al., 1994 *J Leukocyt. Biol.* 55:272, and references cited therein), interleukin-17 (IL-17) (e.g., GenBank Acc. Nos. U32659, U43088) and interleukin-17 receptor (IL-17R) (e.g., GenBank Acc. Nos. U31993, U58917).

As provided herein, an IRAM that is an accessory cell agent refers to a molecule typically produced by any of a number of cell types referred to herein as accessory cells, with which T cells interact during the course of an immune response, including but not limited to monocytes, macrophages, dendritic cells, B cells or any cell capable of antigen presenting cell (APC) function, which may further include by way of illustration and not limitation, keratinocytes, endothelial cells, astrocytes, glial cells, reticuloendothelial cells such as those of the bone marrow, spleen and lymph nodes, fibroblasts, epithelial cells, muscle cells and T cells. As used herein, accessory cells may or may not have been experimentally modified, for example, by gene transfer, to increase their ability to present antigen. IRAM on any of these or other accessory cell types with which T cells interact may include accessory cell surface molecules, secreted accessory cell soluble products or intracellular accessory cell components, that participate in any molecular or cellular event leading to a host immune response. These immune functions may include, for example, intermolecular recognition and/or binding events; immune cell/immunocyte induction and/or activation; immune cell-cell or molecule-cell interactions such as cell stimulation, intercellular signaling, transmembrane or intracellular signal transduction; initiation of specific transcriptional or translational activity; initiation of specific metabolic, catabolic, respiratory, cytoskeletal or motility, mitotic or apoptotic behavior; or any other molecular or cellular event associated with the generation of a host immune response. In certain preferred embodiments these immune functions are associated with APC activity, and in certain other preferred embodiments these immune functions are associated with T lymphocyte activation. Additionally, in certain other preferred embodiments these functions are associated with B lymphocyte stimulation, and in certain other preferred embodiments these functions are associated with intercellular adhesion. According to the present invention, an IRAM that is an accessory cell agent need not naturally be expressed exclusively by accessory cells. Additionally, according to the present invention an IRAM that is an accessory cell agent encoded by a recombinant expression construct of the subject vaccine need not be expressed exclusively by accessory cells of the host immunized using the subject vaccine, regardless of whether or not the accessory cell agent is ordinarily a gene product expressed uniquely in accessory cells, so long as the accessory cell agent encoded by the nucleic acid delivered in the vaccine provided has the effect of qualitatively or quantitatively altering a cell SRA specific immune response.

Thus, in particularly preferred embodiments, the accessory cell agent is an accessory cell surface molecule of known structure and having a known or described function, including but not limited to accessory cell agents having any of the immune cell activation, adhesion, receptor/recognition, enzymatic or other activities described in references cited for the following cell surface receptors: CD59 (e.g., GenBank Acc. Nos. SEG_HUMCD590, M95708, M34671), CD48 (e.g., GenBank Acc. Nos. M59904), CD58/LFA-3 (e.g., GenBank Acc. No. A25933, Y00636, E12817; see also JP 1997075090-A), CD72 (e.g., GenBank Acc. Nos. AA311036, S40777, L35772), CD70(e.g., GenBank Acc. Nos. Y13636, S69339), CD80/B7.1 (Freeman et al., 1989 *J.Immunol.* 43:27 14; Freeman et al., 1991 *J. Exp. Med* 174:625; see also e.g., GenBank Acc. Nos. U33208, 1683379), CD86/B7.2 (Freeman et al., 1993 *J. Exp. Med* 178:2 185, Boriello et al., 1995 *J. Immunol.* 155:5490; see also, e.g., GenBank Acc. Nos. AF099105 (SEQ ID NO: 10), SEG_MMB72G (SEQ ID NOS: 11-15), U39466 (SEQ ID NOS: 16-20), U04343 (SEQ ID NOS: 21-22) SEG_HSB725, L25606 (SEQ ID NOS: 23-24), L25259 (SEQ ID NOS: 25-26)), CD40 ligand (e.g., GenBank Acc. Nos. SEG_HUMCD40L, X67878, X65453, L07414), IL-17 (e.g., GenBank Acc. Nos. U32659, U43088), CD43 (e.g., GenBank Acc. Nos. X52075, J04536) and VLA-4 (α4β7) (e.g., GenBank Acc. Nos. L12002, X16983, L20788, U97031, L24913, M68892, M95632). Accessory cell agents may also include any of the following cell surface receptors typically associated with B cells: CD19 (e.g., GenBank Acc. Nos. SEG_HUMCD19WO, M84371, SEG_MUSCD19W, M62542), CD20 (e.g., GenBank Acc. Nos. SEG_HUMCD20, M62541), CD22 (e.g., GenBank Acc. Nos. 1680629, Y10210, X59350, U62631, X52782, L16928), CD30 ligand (e.g., GenBank Acc. Nos. L09753, M83554), CD37 (e.g., GenBank Acc. Nos. SEG_MMCD37X, X14046, X53517), CD106 (VCAM-1) (e.g., GenBank Acc. Nos. X53051, X67783, SEG_MMVCAM1C, see also U.S. Pat. No. 5,596,090), CD54 (ICAM-1) (e.g., GenBank Acc. Nos. X84737, S82847, X06990, J03132 SEG_MUSICAM0), interleukin-12 (see, e.g., Reiter et al, 1993 *Crit. Rev. Immunol.* 13:1, and references cited therein). Accessory cell agents may also include any of the following cell surface receptors typically associated with dendritic cells: CD83 (e.g., GenBank Acc. Nos. AF001036, AL021918), DEC-205 (e.g., GenBank Acc. Nos. AF011333, U19271).

Without wishing to be bound by theory, the vaccines of the present invention are believed to provide nucleic acid sequences encoding SRA and IRAM (or the SRA and IRAM products themselves) in a manner that favors the elicitation of SRA specific antibody titers of high magnitude, duration and/or quality. It further appears that the subject invention vaccine promotes uptake and expression of the recombinant expression constructs provided herein by host cells that are, or are induced to become, contributors to a host immune response directed against SRA epitopes. Thus one or more cell types in the host may be induced by the subject invention vaccine to express one or more of a SRA and an IRAM that are provided by the vaccine, and in preferred embodiments a SRA and one each of an IRAM that is a T cell agent and an IRAM that is an accessory cell agent. The number of cell types in the host that are influenced to express SRA and/or IRAM may be highly variable. It appears, however, that providing a vaccine capable of directing expression of a SRA and at least one IRAM, and in preferred embodiments two IRAM including a T cell agent and an accessory cell agent, produces the unexpected result of a humoral response directed against the SRA. As such, the present invention vaccine may generate spatiotemporally coordinated expression of (i) a target antigen (SRA), (ii) a stimulus of T lymphocyte activity such as helper T cell function (e.g., T cell agent IRAM) and (iii) a mediator of accessory cell function such as a T cell costimulus (e.g., a second T cell agent or an accessory cell agent IRAM) or an antigen presenting cell activity (e.g., an accessory cell agent IRAM), which may be generally regarded as requirements for optimal antibody responses under certain conditions.

Thus, according to certain particularly preferred embodiments of the invention, there will be certain especially useful combinations of at least two T cell agent IRAM, or of at least one each of a T cell agent IRAM and an accessory cell agent IRAM, that may be encoded along with a desired target SRA by the expression constructs of the subject vaccine. Examples of preferred IRAM that may be used in these combinations are presented in Tables 1 and 2, but it should be understood that the invention is in no way limited to these particular IRAM. Further, it should be understood that any combination of any IRAM as defined herein, regardless of whether such IRAM are included in Tables 1 and 2, is within the scope of the invention, as is any combination of IRAM from within Table 1, from within Table 2, or any other IRAM combination. Moreover, the person having ordinary skill in the art will appreciate that different IRAM combinations may be particularly preferred for different uses as provided herein, such that, as described above, certain of the SRA vaccines are useful for enhancing an immune response (and in particular an antigen-specific humoral immune response) while certain other SRA vaccines will be useful for moderating, suppressing or otherwise regulating an immune response. Using the compositions and methods provided herein, those skilled in the art can readily determine the effect upon an immune response of a particular SRA vaccine by employing routine methodologies.

TABLE 1

IRAM FOR USE IN COMBINATIONS

CD80/B7.1
CD86/B7.2
CD40 ligand
CD58 + CD59
CD106/VCAM-1
CD54/ICAM-1
CD30 ligand

TABLE 2

IRAM FOR USE IN COMBINATIONS 4-1BB ligand
IL-12 (interleukin-12)
IL-4
IFN-γ
IL-17

Thus, in certain preferred embodiments the SRA vaccine includes sequences encoding the IRAM (or the expressed products) 4-1BB ligand and CD86. In another preferred embodiment the SRA vaccine includes sequences encoding the IRAM (or the expressed products) 4-1BB ligand and CD80, and in another preferred embodiment the SRA vaccine includes sequences encoding the IRAM (or the expressed products) 4-1BB ligand and CD86. In other embodiments, the sequences encoding IRAM may encode one or more of a cytokine, a lymphokine or a chemokine, such that these IRAM may be combined with other IRAM provided herein. For example, a SRA vaccine of the present invention may include genes encoding cell surface IRAM such as those of Table 1 in combination with one or more of the soluble IRAM IFN-γ, IL-4, IL-12 or IL-17.

Determination of the induction of an immune response by the vaccines of the present invention may be established by any of a number of well known immunological assays with which those having ordinary skill in the art will be readily familiar. As described above, such assays include, but need not be limited to, to in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (*Immunology Methods Manual: The Comprehensive Sourcebook of Techniques*, 1998; see also *Current Protocols in Immunology*; see also, e.g., Weir, *Handbook of Experimental Immunology*, 1986 Blackwell Scientific, Boston, Mass.; Mishell and Shigii (eds.) *Selected Methods in Cellular Immunology*, 1979 Freeman Publishing, San Francisco, Calif.; Green and Reed, 1998 *Science* 281:1309 and references cited therein.).

Detection of the proliferation of SRA reactive T cells may be accomplished by a variety of known techniques. For example, T cell proliferation can be detected by measuring the rate of DNA synthesis, and SRA specificity can be determined by controlling the stimuli (such as, for example, SRA or control antigen-pulsed antigen presenting cells) to which candidate SRA reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to intact SRA may be quantified.

Detection of SRA specific antibody production may be achieved, for example, by assaying a sample (e.g., an immunoglobulin containing sample such as serum, plasma or blood) from a host treated with a vaccine according to the present invention using in vitro methodologies such as radioimmunoassay (RIA), enzyme linked immunosorbent assays (ELISA), equilibrium dialysis or solid phase immunoblotting including Western blotting. In preferred embodiments ELISA assays may further include antigen-capture immobilization of the SRA target antigen with a solid phase monoclonal antibody specific for the SRA, for example, to enhance the sensitivity of the assay.

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), *Manual of Clinical Laboratory Immunology*, 5$^{th}$ Ed., 1997 American Society of Microbiology, Washington, D.C.

As described above, the present invention provides vaccines comprising recombinant expression vectors capable of directing the expression of SRA and IRAM having amino acid sequences that are known in the art and that are encoded by previously disclosed nucleic acid sequences. The "amino acids," which occur in the various amino acid sequences referred to herein, are identified according to their well known three letter or one letter abbreviations. The nucleotides, which occur in the various DNA sequences or fragments thereof referred herein, are designated with the standard single letter designations used routinely in the art. A given amino acid sequence may also encompass similar amino acid sequences having only minor changes, for example by way of illustration and not limitation, covalent chemical modifications, insertions, deletions and substitutions, which may further include conservative substitutions. Amino acid sequences that are similar to one another may share substantial regions of sequence homology. In like fashion, nucleotide sequences may encompass substantially similar nucleotide sequences having only minor changes, for example by way of illustration and not limitation, covalent chemical modifications, insertions, deletions and substitutions, which may further include silent mutations owing to degeneracy of the genetic code. Nucleotide sequences that are similar to one another may share substantial regions of sequence homology.

As used herein, to "bind to a receptor" refers to the ability of a ligand to specifically recognize and detectably bind to a receptor, as assayed by standard, e.g., in vitro assays.

The present invention further relates to constructs encoding surface receptor antigen (SRA) and immune response altering molecule (IRAM) polypeptides, and in particular to methods for administering recombinant constructs encoding SRA or IRAM ("SRA/IRAM") polypeptides that may be expressed, for example, on the surfaces of cells in a host, as well as fragments, analogs and derivatives of such polypeptides. The terms "fragment," "derivative" and "analog" when referring to SRA/IRAM polypeptides or fusion proteins, refers to any SRA/IRAM polypeptide or fusion protein that retains essentially the same biological function or activity as such polypeptide. Thus, an analog includes a proprotein which can be activated by cleavage of the proprotein portion to produce an active SRA/IRAM polypeptide.

A fragment, derivative or analog of an SRA/IRAM polypeptide or fusion protein, including SRA/IRAM polypeptides or fusion proteins encoded by the cDNAs referred to herein, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the SRA/IRAM polypeptide, including amino acids that are employed for detection or specific functional alteration of the SRA/IRAM polypeptide or a prdprotein sequence. Such fragments, derivatives and analogs are deemed to be within the scope of those skilled in the art from the teachings herein.

The polypeptides of the present invention include SRA/IRAM polypeptides and fusion proteins having amino acid sequences that are identical or similar to sequences known in the art. For example by way of illustration and not limitation, the human HER2 SRA, CD86 IRAM and 4-1BB ligand IRAM polypeptides (HER2: e.g., GenBank Acc. Nos. X03363 (SEQ ID NOS: 5-6), M17730 (SEQ ID NOS: 7-8), SEG_HUMHER20(SEQ ID NO: 9); CD86/B7.2: Freeman et al., 1993 *J. Exp. Med.* 178:2185, Boriello et al., 1995 *J. Immunol.* 155:5490; see also, e.g., GenBank Acc. Nos. AF099105 (SEQ ID NO: 10), SEG_MMB72G (SEQ ID NOS: 11-15), U39466 (SEQ ID NOS: 16-20), U04343 (SEQ ID NO: 21-22), SEG_HSB725, L25606 (SEQ ID NOS: 23-24), L25259 (SEQ ID NOS: 25-26); 4-1BB ligand: Goodwin et al., 1993 *Eur. J. Immunol.* 23:2361; Melero et al., 1998 *Eur. J. Immunol.* 3:116), are contemplated for use according to the instant invention, as are polypeptides having at least 70% similarity (preferably a 70% identity) and more preferably 90% similarity (more preferably a 90% identity) to the reported polypeptides and still more preferably a 95% similarity (still more preferably a 95% identity) to the reported polypeptides and to portions of such polypeptides, wherein such portions of an SRA/IRAM polypeptide generally contain at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide. Fragments or portions of the nucleic acids encoding polypeptides of the present invention may be used to synthesize full-length nucleic acids of the present invention. As used herein, "% identity" refers to the percentage of identical amino acids situated at corresponding amino acid residue positions when two or more polypeptide are aligned and their sequences analyzed using a gapped BLAST algorithm (e.g., Altschul et al., 1997 *Nucl. Ac. Res.* 25:3389) which weights sequence gaps and sequence mismatches according to the default weightings provided by the National Institutes of Health/NCBI database (Bethesda, Md.: see the World Wide Web at ncbi.nlm.nih.gov/cgi-bin/BLAST/nph-newblast).

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

The term "gene" means the segment of DNA involved in producing a polypeptide chain; it includes regions preceding and following the coding region "leader and trailer" as well as intervening sequences (introns) between individual coding segments (exons).

As described herein, the invention provides SRA (or IRAM) fusion proteins encoded by nucleic acids that have the SRA (or IRAM) coding sequence fused in frame to an additional coding sequence to provide for expression of a SRA (or IRAM) polypeptide sequence fused to an additional functional or non-functional polypeptide sequence that permits, for example by way of illustration and not limitation, detection, functional alteration, isolation and/or purification of the SRA (or IRAM) fusion protein. Such SRA (or IRAM) fusion proteins may permit functional alteration by containing additional polypeptide sequences that influence SRA (or IRAM)

behavior, for example by providing a desirable modified SRA (or IRAM) conformation that may enhance or impair particular SRA(or IRAM) interactions with cells and molecules of the immune system, with which it may interact in the course of eliciting an immune response.

For example, by way of illustration and not limitation, in certain SRA/IRAMs it may be desirable to include amino acid sequences (including glycosylation sites where appropriate) that are recognized by intercellular adhesion receptors such as specific leukocyte integrins, selecting, immunoglobulin gene superfamily members, intercellular adhesion molecules (ICAM-1, -2, -3) and the like. In certain instances, such sequences may comprise polypeptide domains having known functions, for example, extracellular domains of cell surface molecules that participate in antigen presentation to T cells or other T cell activation/co-stimulation motifs, as described above. In certain other SRA/IRAM, glycosylation sites for the posttranslational addition of N-linked oligosaccharides (e.g., Asn-X-Ser/Thr) or O-linked oligosacharides (e.g., SerPThr) may be included. For certain other SRA/IRAM encoded by the vaccine constructs contemplated by the present invention, fusion protein domains having desired functional properties can be included that may be, for example by way of illustration and not limitation, transmembrane receptor cytoplasmic domain sequences such as G-protein binding, receptor associated kinase (e.g., fyn, lck, etc.) binding, directly or indirectly cytoskeletal interacting or other signal transducing domains; transmembrane domains; cell surface receptor extracellular domains such as cytokine, growth factor and chemokine binding domains, extracellular matrix receptor domains or tethered ligand receptor (e.g., thrombin receptor) type domains; or any other useful functional polypeptide domain, or a variant thereof.

Thus, any SRA or IRAM encoded by the recombinant expression constructs provided by the present invention for use herein in a vaccine for eliciting sustained high titers of antibodies specific for a cell SRA may be customized for a particular application. Briefly, additions, substitutions and deletions of amino acids may be produced by any commonly employed recombinant DNA method.

Modification of the polypeptide may be effected by any means known to those of skill in this art. The preferred methods herein rely on modification of DNA encoding the polypeptide and expression of the modified DNA. DNA encoding one of the SRA/IRAM discussed above may be mutagenized using standard methodologies, including those described below. For example, cysteine residues that may be useful to facilitate multimer formation or to promote particular molecular conformation can be added to a polypeptide. Conversely, cysteine residues that are responsible for aggregate formation may be deleted or replaced. If necessary, the identity of cysteine residues that contribute to aggregate formation may be determined empirically, by deleting and/or replacing a cysteine residue and ascertaining whether the resulting protein aggregates in solutions containing physiologically acceptable buffers and salts. In addition, fragments of SRA/IRAM may be constructed and used. As noted above, the counterreceptor/ligand binding domains for many candidate SRA/IRAM have been delineated, such that one having ordinary skill in the art may readily select appropriate polypeptide domains for inclusion in the encoded products of the instant vaccine constructs.

Conservative substitutions of amino acids are well-known and may be made generally without altering the biological activity of the resulting SRA or IRAM molecule. For example, such substitutions are generally made by interchanging within the groups of polar residues, charged residues, hydrophobic residues, small residues, and the like. If necessary, such substitutions may be determined empirically merely by testing the resulting modified SRA or IRAM protein for the ability to bind to the appropriate cell surface receptors in in vitro biological assays, or to bind to appropriate antibodies. Those that retain this ability are suitable for use in the vaccines and methods herein.

As noted above, vaccines comprising expression constructs encoding SRA and IRAM that are suitable for use herein are able to induce an immune response in a host that elicits sustained high titers of SRA specific antibodies. However, some SRA or IRAM may have undesirable biological activities, for example those that are mitogens for inappropriate cell types such as cells that do not contribute to the generation of a SRA specific antibody response. When present, the structural region of such a candidate SRA or IRAM responsible for inducing mitogenesis or any other such undesirable biological activity may be altered in a manner that removes the unwanted activity without ablating the ability to induce the desired humoral immunity. Examples of suitable structural alteration may include, but need not be limited to, deletion of one or more nucleotides from the appropriate region of a SRA/IRAM encoding DNA construct, mutation of nucleotides encoding one or more key amino acid residues upon which the unwanted biological activity depends, or genetically removing an entire domain encoding nucleotide sequence to remove the undesirable activity and in its place substituting a functionally innocuous domain encoding sequence.

If the SRA/IRAM has been modified so as to lack particular biological activities, specific antibody binding (e.g., for SRA) and T cell stimulation/co-stimulation or accessory cell function (e.g., for IRAM) may still be readily assayed by antibody assays such as those provided above, or by any of a number of established in vitro assays for IRAM activity that are known in the art and that will further depend on the nature of the particular IRAM.

The vaccines of the present invention also provide constructs encoding SRA/IRAM that may be targeted to a cell membrane, and in particular to a host cell plasma membrane, according to known membrane localization polypeptide motifs which may be naturally present or artificially introduced into the nucleic acid sequences encoding SRA/IRAM. A cell membrane as used herein may be any cellular membrane, and typically refers to membranes that are in contact with cytosolic components, including especially the plasma membrane and also intracellular membrane bounded compartments such as intracellular vesicles, endosomes, lysosomes, receptosomes, ER-Golgi constituents and other organelles. Hence, in preferred embodiments, an SRA/IRAM protein or fusion protein may be targeted to a plasma membrane. In other preferred embodiments, for example, recombinant expression constructs according to the invention vaccine may encode SRA/IRAM proteins fusion proteins that contain polypeptide sequences that direct the fusion protein to be incorporated into a heterologous plasma membrane component, to associate with a specific cytoplasmic component including the cytoplasmic domain of a transmembrane cell surface receptor or to be directed to a particular subcellular location by any of a variety of known intracellular protein sorting mechanisms with which those skilled in the art will be familiar. These and related embodiments are encompassed by the instant compositions and methods directed to targeting a polypeptide of interest to a predefined intracellular, membrane or extracellular localization.

Accordingly, the SRA/IRAM-encoding constructs of the present invention may include genes that encode SRA/IRAM that are secreted, or that are not secreted, or that are targeted for localization to specific subcellular compartments within the cell. Nucleic acid sequences encoding peptides that direct intracellular sorting of newly synthesized polypeptides to secretory pathways or to residence in particular intracellular compartments are known and are within the scope of the present invention.

Thus, for example, nucleic acid constructs that encode SRA/IRAM may contain sequences encoding peptides that direct an encoded SRA/IRAM to be incorporated into the plasma membrane, to be secreted from a cell via the classical ER-Golgi secretory pathway, to associate with a specific cytoplasmic component including the cytoplasmic domain of a transmembrane cell surface receptor or to be directed to a particular subcellular location by a known intracellular protein sorting mechanism with which those skilled in the art will be familiar. Such intracellular protein sorting peptide sequences may also be present in ligands or nucleic acid binding domains that are provided by the present invention.

The present invention further relates to nucleic acids which hybridize to SRA/IRAM encoding polynucleotide sequences as provided herein, as incorporated by reference or as will be readily apparent to those familiar with the art, if there is at least 70%, preferably at least 90%, and more preferably at least 95% identity between the sequences. The present invention particularly relates to nucleic acids which hybridize under stringent conditions to the SRA/IRAM encoding nucleic acids referred to herein. As used herein, the term "stringent conditions" means hybridization will occur only if there is at least 95% and preferably at least 97% identity between the sequences. The nucleic acids which hybridize to SRA/IRAM encoding nucleic acids referred to herein, in preferred embodiments, encode polypeptides which retain substantially the same biological function or activity as the SRA/IRAM polypeptides encoded by the cDNAs of the references cited herein.

As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed. Typically "high", "medium" and "low" stringency encompass the following conditions or equivalent conditions thereto: high stringency: 0.1×SSPE or SSC, 0.1% SDS, 65° C.; medium stringency: 0.2×SSPE or SSC, 0.1% SDS, 50° C.; and low stringency: 1.0 ×SSPE or SSC, 0.1% SDS, 50° C.

The nucleic acids of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes an SRA/IRAM polypeptide for use according to the invention may be identical to the coding sequence known in the art for any given SRA/IRAM, or may be a different coding sequence, which, as a result of the redundancy or degeneracy of the genetic code, encodes the same SRA/IRAM polypeptide.

The nucleic acids which encode SRA/IRAM polypeptides for use according to the invention may include, but are not limited to: only the coding sequence for the SRA/IRAM polypeptide; the coding sequence for the SRA/IRAM polypeptide and additional coding sequence; the coding sequence for the SRA/IRAM polypeptide (and optionally additional coding sequence) and non-coding sequence, such as introns or non-coding sequences 5' and/or 3' of the coding sequence for the SRA/IRAM polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding" a SRA or IRAM encompasses a nucleic acid which includes only coding sequence for a SRA/IRAM polypeptide as well as a nucleic acid which includes additional coding and/or non-coding sequence(s).

Nucleic acids and oligonucleotides for use as described herein can be synthesized by any method known to those of skill in this art (see, e.g., WO 93/01286, U.S. application Ser. No. 07/723,454, now abandoned; U.S. Pat. Nos. 5,218,088; 5,175,269; 5,109,124). Identification of oligonucleotides and nucleic acid sequences for use in the vaccines provided by the present invention involves methods well known in the art. For example, the desirable properties, lengths and other characteristics of useful oligonucleotides are well known. In certain embodiments, synthetic oligonucleotides and nucleic acid sequences may be designed that resist degradation by endogenous host cell nucleolytic enzymes by containing such linkages as: phosphorothioate, methylphosphonate, sulfone, sulfate, ketyl, phosphorodithioate, phosphoramidate, phosphate esters, and other such linkages that have proven useful in antisense applications (see, e.g., Agrwal et al., *Tetrehedron Lett.* 28:3539-3542 (1987); Miller et al., *J. Am. Chem. Soc.* 93:6657-6665 (1971); Stec et al., *Tetrehedron Lett.* 26:2191-2194 (1985); Moody et al., *Nucl. Acids Res.* 12:4769-4782 (1989); Uznanski et al., *Nucl. Acids Res.* (1989); Letsinger et al., *Tetrahedron* 40:137-143 (1984); Eckstein, *Annu. Rev. Biochem.* 54:367-402 (1985); Eckstein, *Trends Biol. Sci.* 14:97-100 (1989); Stein In: *Oligodeoxynucleotides. Antisense Inhibitors of Gene Expression*, Cohen, Ed, Macmillan Press, London, pp. 97-117 (1989); Jager et al., *Biochemistry* 27:7237-7246 (1988)).

In one embodiment, the present invention provides truncated cell SRA and/or IRAM, and in another aspect the invention provides nucleic acids encoding truncated cell SRA and/ or IRAM. A truncated molecule may be any molecule that comprises less than a full length version of the molecule. Truncated molecules provided by the present invention may include truncated biological polymers, and in preferred embodiments of the invention such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-fimctional sequences. In other preferred embodiments, truncated molecules are polypeptides that comprise less than the full length amino acid sequence of a particular protein. As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-1500 contiguous nucleotide or amino acid residues, preferably 1-500 contiguous nucleotide or amino acid residues and more preferably 1-300 contiguous nucleotide or amino acid residues. In certain particularly preferred embodiments truncated nucleic acid molecules may have a deletion of 270-330 contiguous nucleotides. In certain other particularly preferred embodiments truncated polypeptide molecules may have a deletion of 80-140 contiguous amino acids.

The present invention further relates to variants of the herein referenced nucleic acids which encode fragments, analogs and/or derivatives of a SRA/IRAM polypeptide. The variants of the nucleic acids encoding SRA/IRAM may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded SRA/IRAM polypeptide.

Variants and derivatives of SRA/IRAM may be obtained by mutations of nucleotide sequences encoding SRA/IRAM polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques*, Jan. 12-19, 1985); Smith et al. (*Genetic Engineering: Principles and Methods BioTechniques*, Jan. 12-19, 1985); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

As an example, modification of DNA may be performed by site-directed mutagenesis of DNA encoding the protein combined with the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest (e.g., a given SRA or IRAM). An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may. be expressed recombinantly in appropriate host cells to produce the modified protein.

Equivalent DNA constructs that encode various additions or substitutions of amino acid residues or sequences, or deletions of terminal or internal residues or sequences not needed for biological activity are also encompassed by the invention. For example, sequences encoding Cys residues that are not essential for biological activity can be altered to cause the Cys residues to be deleted or replaced with other amino acids, preventing formation of incorrect intramolecular disulfide bridges upon renaturation.

Host organisms include those organisms in which recombinant production of SRA/IRAM products encoded by the recombinant constructs of the present invention vaccines may occur, such as bacteria (for example, *E. coli*), yeast (for example, *Saccharomyces cerevisiae* and *Pichia pastoris*), insect cells and mammals, including in vitro and in vivo expression. Host organisms thus may include organisms for the construction, propagation, expression or other steps in the production of the vaccines provided herein; hosts also include subjects in which immune responses take place, as described above. Presently preferred host organisms are *E. coli* bacterial strains, inbred murine strains and murine cell lines, and human cells, subjects and cell lines.

The DNA construct encoding the desired SRA/IRAM is introduced into a plasmid for expression in an appropriate-host. In preferred embodiments, the host is a bacterial host. The sequence encoding the ligand or nucleic acid binding domain is preferably codon-optimized for expression in the particular host. Thus, for example, if a human SRA/IRAM is expressed in bacteria, the codons would be optimized for bacterial usage. For small coding regions, the gene can be synthesized as a single oligonucleotide. For larger proteins, splicing of multiple oligonucleotides, mutagenesis, or other techniques known to those in the art may be used. The sequences of nucleotides in the plasmids that are regulatory regions, such as promoters and operators, are operationally associated with one another for transcription. The sequence of nucleotides encoding a SRA or IRAM chimera (fusion protein) may also include DNA encoding a secretion signal, whereby the resulting peptide is a precursor protein. The resulting processed protein may be recovered from the periplasmic space or the fermentation medium.

In preferred embodiments, the DNA plasmids also include a transcription terminator sequence. As used herein, a "transcription terminator region" is a sequence that signals transcription termination. The entire transcription terminator may be obtained from a protein-encoding gene, which may be the same or different from the inserted SRA/IRAM encoding gene or the source of the promoter. Transcription terminators are optional components of the expression systems herein, but are employed in preferred embodiments.

The plasmids used herein include a promoter in operative association with the DNA encoding the protein or polypeptide of interest and are designed for expression of proteins in a suitable host as described above (e.g., bacterial, murine or human) depending upon the desired use of the plasmid (e.g., administration of a vaccine containing SRA/IRAM encoding sequences, or of a vaccine containing expressed SRA/IRAM products). Suitable promoters for expression of proteins and polypeptides herein are widely available and are well known in the art. Inducible promoters or constitutive promoters that are linked to regulatory regions are preferred. Such promoters include, but are not limited to, the T7 phage promoter and other T7-like phage promoters, such as the T3, T5 and SP6 promoters, the trp, lpp, and lac promoters, such as the lacUV5, from *E. coli*; the P10 or polyhedrin gene promoter of baculovirus/insect cell expression systems (see, e.g., U.S. Pat. Nos. 5,243,041, 5,242,687, 5,266,317, 4,745,051, and 5,169,784) and inducible promoters from other eukaryotic expression systems. For expression of the proteins such promoters are inserted in a plasmid in operative linkage with a control region such as the lac operon.

Preferred promoter regions are those that are inducible and functional in *E. coli*. Examples of suitable inducible promoters and promoter regions include, but are not limited to: the *E. coli* lac operator responsive to isopropyl β-D-thiogalactopyranoside (IPTG; see Nakamura et al., *Cell* 18:1109-1117, 1979); the metallothionein promoter metal-regulatory-elements responsive to heavy-metal (e.g., zinc) induction (see, e.g., U.S. Pat. No. 4,870,009 to Evans et al.); the phage T7lac promoter responsive to IPTG (see, e.g., U.S. Pat. No. 4,952, 496; and Studier et al., *Meth. Enzymol.* 185:60-89, 1990) and the TAC promoter.

The plasmids may optionally include a selectable marker gene or genes that are functional in the host. A selectable marker gene includes any gene that confers a phenotype on bacteria that allows transformed bacterial cells to be identified and selectively grown from among a vast majority of untransformed cells. Suitable selectable marker genes for bacterial hosts, for example, include the ampicillin resistance gene ($Amp^r$), tetracycline resistance gene ($Tc^r$) and the kanamycin resistance gene ($Kan^r$). The kanamycin resistance gene is presently preferred.

The plasmids may also include DNA encoding a signal for secretion of the operably linked protein. Secretion signals suitable for use are widely available and are well known in the art. Prokaryotic and eukaryotic secretion signals functional in *E. coli* may be employed. The presently preferred secretion signals include, but are not limited to, those encoded by the following *E. coli* genes: ompA, ompT, ompF, ompC, beta-lactamase, and alkaline phosphatase, and the like (von Heijne, *J. Mol Biol.* 184:99-105, 1985). In addition, the bacterial pelB gene secretion signal (Lei et al., *J. Bacteriol.* 169:4379, 1987), the phoA secretion signal, and the cek2 functional in insect cell may be employed. The most preferred secretion signal is the *E. coli* ompA secretion signal. Other prokaryotic and eukaryotic secretion signals known to those of skill in the art may also be employed (see, e.g., von Heijne, *J. Mol. Biol.* 184:99-105, 1985). Using the methods described herein, one of skill in the art can substitute secretion signals that are functional in either yeast, insect or mammalian cells to secrete proteins from those cells.

Particularly preferred plasmids for transformation of *E. coli* cells include the pET expression vectors (e.g., pET-11a, pET-12a-c, pET-15b; see U.S. Pat. No. 4,952,496; available from Novagen, Madison, Wis.)

Other preferred plasmids include the pKK plasmids, particularly pKK 223-3, which contains the tac promoter (Brosius et al., *Proc. Natl. Acad. Sci.* 81:6929, 1984; Ausubel et al., *Current Protocols in Molecular Biology*; U.S. Pat. Nos. 5,122,463, 5,173,403, 5,187,153, 5,204,254, 5,212,058, 5,212,286, 5,215,907, 5,220,013, 5,223,483, and 5,229,279). Plasmid pKK has been modified by replacement of the ampicillin resistance gene with a kanamycin resistance gene. (Available from Pharmacia; obtained from pUC4K, see, e.g., Vieira et al. (*Gene* 19:259-268, 1982; and U.S. Pat. No. 4,719, 179.) Baculovirus vectors, such as pBlueBac (also called pJVETL and derivatives thereof), particularly pBlueBac III (see, e.g., U.S. Pat. Nos. 5,278,050, 5,244,805, 5,243,041, 5,242,687, 5,266,317, 4,745,051, and 5,169,784; available from Invitrogen, San Diego) may also be used for expression of the polypeptides in insect cells. Other plasmids include the pIN-IIIompA plasmids (see U.S. Pat. No. 4,575,013; see also Duffaud et al., *Meth. Enz.* 153:492-507, 1987), such as pIN-IIIompA2.

Preferably, the DNA molecule is replicated in bacterial cells, preferably in *E. coli*. The preferred DNA molecule also includes a bacterial origin of replication, to ensure the maintenance of the DNA molecule from generation to generation of the bacteria. In this way, large quantities of the DNA molecule can be produced by replication in bacteria. Preferred bacterial origins of replication include, but are not limited to, the fl-ori and col E1 origins of replication. Preferred hosts contain chromosomal copies of DNA encoding T7 RNA polymerase operably linked to an inducible promoter, such as the lacUV promoter (see U.S. Pat. No. 4,952, 496). Such hosts include, but are not limited to, lysogens *E. coli* strains HMS174(DE3)pLysS, BL21(DE3)pLysS, HMSI74(DE3) and BL21(DE3). Strain BL21(DE3) is preferred. The pLys strains provide low levels of T7 lysozyme, a natural inhibitor of T7 RNA polymerase.

The DNA molecules provided may also contain a gene coding for a repressor protein. The repressor protein is capable of repressing the transcription of a promoter that contains sequences of nucleotides to which the repressor protein binds. The promoter can be derepressed by altering the physiological conditions of the cell. For example, the alteration can be accomplished by adding to the growth medium a molecule that inhibits the ability to interact with the operator or with regulatory proteins or other regions of the DNA or by altering the temperature of the growth media. Preferred repressor proteins include, but are not limited to the *E. coli* lacl repressor responsive to IPTG induction, the temperature sensitive λ cI857 repressor, and the like. The *E. coli* lacI repressor is preferred.

In general, recombinant constructs of the subject invention vaccines will also contain elements necessary for transcription and translation. In particular, such elements are preferred where the vaccine is a recombinant expression construct containing nucleic acid sequences encoding SRA/IRAM for expression in the host in which a humoral immune response is desired. In certain embodiments of the present invention, cell type preferred or cell type specific expression of a cell SRA/IRAM encoding gene may be achieved by placing the gene under regulation of a promoter. The choice of the promoter will depend upon the cell type to be transformed and the degree or type of control desired. Promoters can be constitutive or active and may further be cell type specific, tissue specific, individual cell specific, event specific, temporally specific or inducible. Cell-type specific promoters and event type specific promoters are preferred. Examples of constitutive or nonspecific:promoters include the SV40 early promoter (U.S. Pat. No. 5,118,627), the SV40 late promoter (U.S. Pat. No. 5,118,627), CMV early gene promoter (U.S. Pat. No. 5,168,062), and adenovirus promoter. In addition to viral promoters, cellular promoters are also amenable within the context of this invention. In particular, cellular promoters for the so-called housekeeping genes are useful. Viral promoters are preferred, because generally they are stronger promoters than cellular promoters. Promoter regions have been identified in the genes of many eukaryotes including higher eukaryotes, such that suitable promoters for use in a particular host can be readily selected by those skilled in the art.

Inducible promoters may also be used. These promoters include MMTV LTR (PCT WO 91/13160), inducible by dexamethasone; metallothionein promoter, inducible by heavy metals; and promoters with cAMP response elements, inducible by cAMP. By using an inducible promoter, the nucleic acid sequence encoding SRA/IRAM may be delivered to a cell by the subject invention vaccine and will remain quiescent until the addition of the inducer. This allows further control on the timing of production of the gene product.

Event-type specific promoters are active or up-regulated only upon the occurrence of an event, such as tum6rigenicity or viral infection. The HIV LTR is a well known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed when a particular SRA/IRAM gene is expressed may be used. This type of promoter is especially useful when one knows the pattern of gene expression relevant to induction of an immune response m a particular tissue of the immune system, so that specific immunocompetent cells within that tissue may be activated or otherwise recruited to participate in an immune response.

In addition to the promoter, repressor sequences, negative regulators, or tissue-specific silencers may be inserted to reduce non-specific expression of SRA/IRAM in certain situations, such as, for example, a host that is transiently imrmunocompromised as part of a therapeutic strategy. Multiple repressor elements may be inserted in the promoter region. Repression of transcription is independent on the orientation of repressor elements or distance from the promoter. One type of repressor sequence is an insulator sequence. Such sequences inhibit transcription (Dunaway et al., *Mol Cell Biol* 17: 182-9, 1997; Gdula et al., *Proc Natl Acad Sci USA* 93:9378-83, 1996, Chan et al., *J. Virol* 70: 5312-28, 1996; Scott and Geyer, *EMBO J* 14:6258-67, 1995; Kalos and Fournier, *Mol Cell Biol* 15:198-207, 1995; Chung et al., *Cell* 74: 505-14, 1993) and will silence background transcription.

Repressor elements have also been identified in the promoter regions of the genes for type II (cartilage) collagen, choline acetyltransferase, albumin (Hu et al., *J. Cell Growth Differ.* 3(9):577-588, 1992), phosphoglycerate kinase (PGK-2) (Misuno et al., *Gene* 119(2):293-297, 1992), and in the 6-phosphofructo-2-kinase/fructose-2, 6-bisphosphatase gene. (Lemaigre et al., *Mol. Cell Biol.* 11(2):1099-1106.) Furthermore, the negative regulatory element Tse-1 has been identified in a number of liver specific genes, and has been shown to block cAMP response element-(CRE) mediated induction of gene activation in hepatocytes. (Boshart et al., *Cell* 61(5):905-916, 1990).

In preferred embodiments, elements that increase the expression of the desired product are incorporated into the construct. Such elements include internal ribosome binding sites (IRES; Wang and Siddiqui, *Curr. Top. Microbiol. Immunol* 203:99, 1995; Ehrenfeld and Semler, *Curr. Top. Microbiol. Immunol.* 203:65, 1995; Rees et al., *Biotechniques* 20:102, 1996; Sugimoto et al., *Biotechnology* 12:694, 1994). IRES increase translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, RNase probe protection and the like. Protein levels may be assayed by any known method, including ELISA, western blot, immunocytochemistry or other well known techniques.

Other elements may be incorporated into the SRA/IRAM vaccine constructs of the present invention. In preferred embodiments, the construct includes a transcription terminator sequence, including a polyadenylation sequence, splice donor and acceptor sites, and an enhancer. Other elements useful for expression and maintenance of the construct in mammalian cells or other eukaryotic cells may also be incorporated (e.g., origin of replication). Because the constructs are conveniently produced in bacterial cells, elements that are necessary for, or that enhance, propagation in bacteria are incorporated. Such elements include an origin of replication, a selectable marker and the like.

As provided herein, an additional level of controlling the expression of nucleic acids encoding SRA/IRAM delivered to cells using the constructs of the invention vaccines may be provided by simultaneously delivering two or more differentially regulated nucleic acid constructs. The use of such a multiple nucleic acid construct approach may permit coordinated regulation of an immune response such as, for example, spatiotemporal coordination that depends on the cell type arid/or presence of another expressed vaccine encoded component. Those familiar with the art will appreciate that multiple levels of regulated gene expression may be achieved in a similar manner by selection of suitable regulatory sequences, including but not limited to promoters, enhancers and other well known gene regulatory elements.

The present invention also relates to vectors, and to constructs prepared from known vectors that include nucleic acids of the present invention, and in particular to "recombinant expression constructs" that include any nucleic acids encoding SRA/IRAM polypeptides according to the invention as provided above; to host cells which are genetically engineered with vectors and/or constructs of the invention and to methods of administering vaccines comprising nucleic acid sequences encoding such SRA/IRAM polypeptides and fusion proteins of the invention, or fragments or variants thereof, by recombinant techniques. SRA/IRAM proteins can be expressed in virtually any host cell under the control of appropriate promoters, depending on the nature of the construct (e.g., type of promoter, as described above), and on the nature of the desired host cell (e.g., whether postmitotic terminally differentiated or actively dividing; e.g., whether the expression construct occurs in host cell as an episome or is integrated into host cell genome). Appropriate cloning and expression vectors for use with prokaryotic and eukaryotic hosts are described by Sambrook, et al., *Molecular Cloning: A Laboratory Manual*, Second Edition, Cold Spring Harbor, N.Y., (1989).

Typically, the constructs are derived from plasmid vectors. A preferred construct is a modified pNASS vector (Clontech, Palo Alto, Calif.), which has nucleic acid sequences encoding an ampicillin resistance gene, a polyadenylation signal and a T7 promoter site. Other suitable mammalian expression vectors are well known (see, e.g., Ausubel et al., 1995; Sambrook et al., supra; see also, e.g., catalogues from Invitrogen, San Diego, Calif.; Novagen, Madison, Wis.; Pharmacia, Piscataway, N.J.; and others). Presently preferred constructs are prepared from the pLNCX plasmid (Clontech, Palo Alto, Calif.).

Generally, recombinant expression vectors will include origins of replication and selectable markers permitting transformation of the host cell, and a promoter derived from a highly-expressed gene to direct transcription of a downstream structural sequence, as described above. The heterologous structural sequence is assembled in appropriate phase with translation initiation and termination sequences. Thus, for example, the SRA/IRAM encoding nucleic acids as provided herein may be included in any one of a variety of expression vector constructs as a recombinant expression construct for expressing an SRA/IRAM polypeptide in a host cell. In preferred embodiments the constructs are included in vaccines that are administered in vivo. Such vectors and constructs include chromosomal, nonchromosomal and synthetic DNA sequences, e.g., derivatives of SV40; bacterial plasmids; phage DNA; yeast plasmids; vectors derived from combinations of plasmids and phage DNA, viral DNA, such as vaccinia, adenovirus, fowl pox virus, and pseudorabies, or replication deficient retroviruses as described below. However, any other vector may be used for preparation of a recombinant expression construct, and in preferred embodiments such a vector will be replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.); Glover (Ed.) (1985 *DNA Cloning Vol. I and II*, IRL Press, Oxford, UK); Hames and Higgins (Eds.), (1985 *Nucleic Acid Hybridization*, IRL Press, Oxford, UK); and elsewhere.

The DNA sequence in the expression vector is operatively linked to at least one appropriate expression control sequences (e.g., a constitutive promoter or a regulated promoter) to direct mRNA synthesis. Representative examples of such expression control sequences include promoters of eukaryotic cells or their viruses, as described above. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding an SRA/IRAM polypeptide is described herein.

Transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

As provided herein, in certain embodiments the vector may be a viral vector such as a retroviral vector. (Miller et al., 1989 *BioTechniques* 7:980; Coffin and Varmus, 1996 Retroviruses, Cold Spring Harbor Laboratory Press, NY.) For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

Retroviruses are RNA viruses which can replicate and integrate into the genome of a host cell via a DNA intermediate. This DNA intermediate, or provirus, may be stably integrated into the host cell DNA. According to certain embodiments of the present invention, a vaccine may comprise a retrovirus into which a foreign gene that encodes a foreign protein is incorporated in place of normal retroviral RNA. When retroviral RNA enters a host cell coincident with infection, the foreign gene is also introduced into the cell, and may then be integrated into host cell DNA as if it were part of the retroviral genome. Expression of this foreign gene within the host results in expression of the foreign protein.

Most retroviral vector systems which have been developed for gene therapy are based on murine retroviruses. Such retroviruses exist in two forms, as free viral particles referred to as virions, or as proviruses integrated into host cell DNA. The virion form of the virus contains the structural and enzymatic proteins of the retrovirus (including the enzyme reverse transcriptase), two RNA copies of the viral genome, and portions of the source cell plasma membrane containing viral envelope glycoprotein. The retroviral genome is organized into four main regions: the Long Terminal Repeat (LTR), which contains cis-acting elements necessary for the initiation and termination of transcription and is situated both 5' and 3' of the coding genes, and the three coding genes gag, pol, and env. These three genes gag, pol, and env encode, respectively, internal viral structures, enzymatic proteins (such as integrase), and the envelope glycoprotein (designated gp70 and p15e) which confers infectivity and host range specificity of the virus, as well as the "R" peptide of undetermined function.

Separate packaging cell lines and vector producing cell lines have been developed because of safety concerns regarding the uses of retroviruses, including their use in vaccines as provided by the present invention. Briefly, this methodology employs the use of two components, a retroviral vector and a packaging cell line (PCL). The retroviral vector contains long terminal repeats (LTRs), the foreign DNA to be transferred and a packaging sequence (y). This retroviral vector will not reproduce by itself because the genes which encode structural and envelope proteins are not included within the vector genome. The PCL contains genes encoding the gag, pol, and env proteins, but does not contain the packaging signal "y". Thus, a PCL can only form empty virion particles by itself. Within this general method, the retroviral vector is introduced into the PCL, thereby creating a vector-producing cell line (VCL). This VCL manufactures virion particles containing only the retroviral vector's (foreign) genome, and therefore has previously been considered to be a safe retrovirus vector for therapeutic use.

"Retroviral vector construct" refers to an assembly which is, within preferred embodiments of the invention, capable of directing the expression of a sequence(s) or gene(s) of interest, such as SkAuRAM encoding nucleic acid sequences. Briefly, the retroviral vector construct must include a 5' LTR, a mRNA binding site, a packaging signal, an origin of second strand DNA synthesis and a 3' LTR. A wide variety of heterologous sequences may be included within the vector construct, including for example, sequences which encode a protein (e.g., cytotoxic protein, disease-associated antigen, immune accessory molecule, or replacement gene), or which are useful as a molecule itself (e.g., as a ribozyme or antisense sequence).

Retroviral vector constructs of the present invention may be readily constructed from a wide variety of retroviruses, including for example, B, C, and D type retroviruses as well as spumaviruses and lentiviruses (see, e.g., RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Any of the above retroviruses may be readily utilized in order to assemble or construct retroviral vector constructs, packaging cells, or producer cells of the present invention given the disclosure provided herein, and standard recombinant techniques (e.g., Sambrook et al, *Molecular Cloning: A Laboratory Manual,* 2d ed., Cold Spring Harbor Laboratory Press, 1989; Kunkle, *PNAS* 82:488, 1985).

Suitable promoters for use in viral vectors generally may include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

As described above, the retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* 1:5-14 (1990). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the SRA/IRAM polypeptides or fusion proteins. Such retroviral vector particles then may be employed, to transduce eukaryotic cells, either in vitro or in vivo. The transduced eukaryotic cells will express the nucleic acid sequence(s) encoding the SRA/IRAM polypeptide or fusion protein. Eukaryotic cells which may be transduced include, but are not limited to, embryonic stem cells, as well as hematopoietic stem cells, hepatocytes, fibroblasts, circulating peripheral blood mononuclear and polymorphonuclear cells including myelomonocytic cells, lymphocytes, myoblasts, tissue macrophages, dendritic cells, Kupffer cells, lymphoid and reticuloendothelia cells of the lymph nodes and spleen, keratinocytes, endothelial cells, and bronchial epithelial cells.

As another example of an embodiment of the invention in which a viral vector is used to prepare the recombinant SRA/IRAM expression construct, in one preferred embodiment, host cells tansduced by a recombinant viral construct directing the expression of SRA/IRAM polypeptides or fusion proteins may produce viral particles containing expressed SRA/IRAM polypeptides or fusion proteins that are derived from portions of a host cell membrane incorporated by the viral particles during viral budding.

In another aspect, the present invention relates to host cells containing the above described recombinant SRA/IRAM expression constructs. Host cells are genetically engineered (transduced, transformed or transfected) with the vectors and/or expression constructs of this invention which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding SRA/IRAM polypeptides or SRA/IRAM fusion proteins. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella tvphimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of SRA/IRAM expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

The present invention vaccines for eliciting or enhancing titers of antibodies specific for a cell SRA may be formulated into pharmaceutical compositions for administration according to well known methodologies. Pharmaceutical compositions generally comprise one or more recombinant expression constructs, and/or expression products of such constructs, in combination with a pharmaceutically acceptable carrier, excipient or diluent. Such carriers will be nontoxic to recipients at the dosages and concentrations employed. For nucleic acid-based vaccines, or for vaccines comprising expression products of the subject invention recombinant constructs, about 0.01 µg/kg to about 100 mg/kg body weight will be adminstered, typically by the intradermal, subcutaneous, intramuscular or intravenous route, or by other routes. A preferred dosage is about 1 µg/kg to about 1 mg/kg, with about 5 µg/kg to about 200 µg/kg particularly preferred. It will be evident to those skilled in the art that the number and frequency of administration will be dependent upon the response of the host. "Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The pharmaceutical compositions that contain one or more SRA/IRAM encoding constructs (or their expressed products) may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more SRA/IRAM construct or expressed product, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

It may also be desirable to include other components in the vaccine, such as delivery vehicles including but not limited to aluminum salts, water-in-oil emulsions, biodegradable oil vehicles, oil-in-water emulsions, biodegradable microcapsules, and liposomes. Examples of immunostimulatory substances (adjuvants) for use in such vehicles include N-acetyl-muramyl-L-aianine-D-isoglutamine (MDP), lipopolysaccharides (LPS), glucan, IL-12, GM-CSF, gamma interferon and IL-15.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions (including vaccines) may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

As described above, the subject invention includes compositions capable of delivering nucleic acid molecules encoding cell SRA and IRAM. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616-627, 1988; Li et al., *Hum. Gene Ther.* 4:403-409, 1993; Vincent et al., *Nat. Genet.* 5:130-134, 1993; and Kolls et al., *Proc. Natl. Acad. Sci. USA* 91:215-219, 1994), pox virus (see U.S. Pat. No. 4,769,330; U.S. Pat. No. 5,017,487; and WO 89/01973)), recombinant expression construct nucleic acid molecules complexed to a polycationic molecule (see WO 93/03709), and nucleic acids associated with liposomes (see Wang et al., *Proc. Natl. Acad. Sci. USA* 84:7851, 1987). In certain embodiments, the DNA may be liked to killed or inactivated adenovirus (see Curiel et al., *Hum. Gene Ther.* 3:147-154, 1992; Cotton et al., *Proc. Natl. Acad. Sci. USA* 89:6094, 1992). Other suitable compositions include DNA-ligand (see Wu et al., *J. Biol. Chem.* 264:16985-16987, 1989) and lipid-DNA combinations (see Felgner et al., *Proc. Natl. Acad. Sci. USA* 84:7413-7417, 1989).

In addition to direct in vivo procedures, ex vivo procedures may be used in which cells are removed from a host, modified, and placed into the same or another host animal. It will be evident that one can utilize any of the compositions noted above for introduction of cell SRA/IRAM encoding nucleic acid molecules into tissue cells in an ex vivo context. Protocols for viral, physical and chemical methods of uptake are well known in the art.

Accordingly, the present invention is useful for enhancing or eliciting, in a host, a patient or in cell culture, a humoral immune response (e.g., the generation of SRA specific antibody forming cells and/or of SRA specific helper T cells that promote humoral immunity). As used herein, the term "patient" refers to any warm-blooded animal, preferably a human. A patient may be afflicted with cancer, such as breast cancer, or may be normal (i.e., free of detectable disease and infection). A "cell culture" is any preparation containing immunocompetent cells or isolated cells of the immune system (including, but not limited to, T cells, macrophages, mdnocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with a cell SRA associated malignancy, and may be reintroduced into a patient after treatment.

A liquid composition intended for either parenteral or oral administration should contain an amount of SRA/IRAM construct or expressed product such that a suitable dosage will be obtained. Typically, this amount is at least 0.01 wt% of an SRA/IRAM construct or expressed product in the composition. When intended for oral administration, this amount may be varied to be between 0.1 and about 70% of the weight of the composition. Preferred oral compositions contain between about 4% and about 50% of SRA/IRAM construct or expressed product(s). Preferred compositions and preparations are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the SRA/IRAM construct or expressed product of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

In the methods of the invention, the SRA/IRAM encoding constructs or expressed product(s) may be administered through use of insert(s), bead(s), timed-release formulation(s), patch(es) or fast-release formulation(s).

The following examples are included for illustrative purposes only and are not intended to limit the scope of the invention.

EXAMPLES

Example 1

Construction Of Surface Antigen Receptor Vaccine Recombinant Expression Vectors

This Example describes the construction of four recombinant expression constructs using the pLNCX plasmid (Clontech, Palo Alto, Calif.) for use in the vaccines of the present invention. Plasmid isolation, production of competent cells, transformation and plasmid manipulations were carried out according to published procedures (Sambrook et al., *Molecular Cloning, a Laboratory Manual*, Cold Spring Harbor Laboratory Press, Cold Spring Harbor, N.Y., 1989; Ausubel et al., 1994 *Current Protocols in Molecular Biology*, 1994 Greene Publishing & John Willey & Sons, NY). Purification of DNA fragments was achieved using the Qiagen Plasmid Maxi Kit (Qiagen, Inc., Valencia, Calif.) according to the manufacturer's recommendations.

The pLNCX plasmid is derived from a Moloney murine leukemia virus (MoMuLV) retroviral vector and includes a cytomegalovirus (CMV) promoter upstream of a multiple cloning site, plus ampicillin resistance and neomycin resistance genes. (Miller et al., 1989 *BioTechniques* 7:980; Coffin and Varmus, 1996 Retroviruses, Cold Spring Harbor Laboratory Press, NY.) In addition to the unaltered control pLNCX plasmid, four pLNCX-derived recombinant plasmid constructs were prepared for DNA vaccination experiments: pLNCX-4-1BBlig, pLNCX-B7.1, pLNCX-B7.2 and pLNCX-Rat-Neu.

pLNCX-4-1BBlig: The pLNCX-4-1BBlig construct was made by digesting pLXSHD containing an inserted DNA sequence encoding the murine 4-1BB ligand (Melero et al., 1998 *Eur. J Immunol* 3:1116) with Sfil and EcoRI to remove the 4-1BB ligand encoding insert, and cloning the recovered 4-1BB insert into Hpa I-cut pLNCX vector.

pLNCX-B7.1: To obtain cDNA sequences encoding murine B7.1 (Freeman et al., 1991 *J. Exp. Med.* 174:625), RNA was isolated from murine splenocytes cultured for 5 days in the presence of the mitogen concanavalin A (ConA) to induce lymphoblasts. The RNA was reverse transcribed using reverse transcriptase and the cDNA products amplified using polymerase chain reaction (PCR) amplification with the following primers:

5'mB7 1. CTAAGCTTATGGCTTGCAATTGTCAGTTG [SEQ ID NO:1]

3'mB7 1. GTATCGATCTAAAGGAAGACGGTCTGTTC [SEQ ID NO:2]

Amplification reactions contained 1 µl of cDNA in a final volume of 50 µl containing 10 mM Tris-HCl (pH 8.3), 50 mM KCl, 0.01% gelatin, 2 mM MgCl$_2$, 0.2 mM dNTPs, and 0.8 µg of each primer. Next, 2.5 U TaqI DNA polymerase (Boehringer Mannheim, Indianapolis, Ind.). Incubations were done in a Peltier PTC-200 Thermal Cycler (M J Research, Inc., Watertown, Mass.). Cycles include a denaturation step (94° C. for 3 min) followed by ten cycles of: 94° C. for 1 min, 48° C. for 1 min, and 72° C. for 1 min; then twenty cycles of: 94° C. for 1 min, 65° C. for 1 min, and 72° C. for 1 min.

The amplified DNA was gel purified and digested with Cla I and Hind III, and then cloned into pLNCX that had first been cut using Cla I and Hind III, to yield the pLNCX-B7.1 recombinant expression construct.

pLNCX-B7.2: For cDNA encoding murine B7.2i (Borriello et al., 1995 *J. Immunol* 155:5490), RNA from 5-day ConA lymphoblasts was isolated and reverse transcribed and the cDNA products amplified by PCR as described above except using the following primers:

```
5'mB7 2.  CGAAGCTTGTTCCAGAACTTACGGAAG  [SEQ ID NO:3]
3'mB7 2.  CGATCGATCTTTCCTCAGGCTCTCAC   [SEQ ID NO:4]
```

The amplified DNA is gel purified and digested with Cla I and then cloned into pLNCX that had first been cut using HpaI, to yield the pLNCX-B7.1 recombinant expression construct.

pLNCX-Rat-Neu: The pLNCX-Rat-Neu construct was made by digesting pSV2 containing an inserted DNA sequence encoding the rat Neu surface receptor antigen (Bargmann et al., 1986 Cell 45:649) with HindIII and AflIII to remove the rat Neu encoding insert, and cloning the recovered Neu insert into Hpa I-cut pLNCX vector.

Example 2

Immunization Of Mice Using Surface Antigen Receptor DNA Vaccines

Specific Pathogen-Free (SPF) breeder FVB/N-TgN (MMTVneu) mice were purchased from Jackson Laboratory (Bar Harbor, Me.) and maintained as a breeder colony at the University of Washington animal care facility (Seattle, Wash.) under SPF conditions. This genetically engineered mouse strain is trarsgenic for and expresses the rat Neu2 transgene under the control of a murine mammary tumor virus (MMTV LTR) promoter, and spontaneous mammary tumors appear in the majority of such mice, albeit only with advanced age (7-12 months).

For immunization with the recombinant expression construct DNA vaccines, female FVB/N-TgN (MMTVneu) mice were used. Plasmid DNA for DNA vaccination was prepared from the constructs described in Example 1 (including pLNCX) using the Qiagen Plasmid Maxi Kit (Qiagen Inc., Valencia, Calif.) according to the manufacturer's instructions. Prior to vaccination, the DNA was dissolved in sterile water. Seven groups, each containing five mice (12 to 15 weeks old) were vaccinated with 25 µg of each indicated plasmid DNA diluted in PBS (GibcoBRL, Grand Island, N.Y.) and adjusted to a final volume of 100 µl with physiological saline (Fujisawa, Inc., Deerfield, Ill.) for injection. Control (pLNCX), SRA (LNCX-Rat-Neu) and IRAM (pLNCX-4-1Bblig, pLNCX-B7.1, pLNCX-B7.2) encoding constructs were used in vaccines as indicated below. Primary immunization was by intradermal injection in the top flank area, and was followed 15 days later by an identical booster injection. At the time of the booster injection, animals also received a dorsal subcutaneous challenge with $2\times10^6$ FVB/N-TgN (MMTVneu) 220 mammary tumor cells from aged mice prepared as described below.

The groups were as follows:

| Group | Component Vaccine DNA Constructs |
|---|---|
| 1. | pLNCX |
| 2. | pLNCX-Rat-Neu |
| 3. | pLNCX-Rat-Neu + pLNCX-B7.1 |
| 4. | pLNCX-Rat-Neu + pLNCX-B7.2 |
| 5. | pLNCX-Rat-Neu + pLNCX-4-1Bblig |
| 6. | pLNCX-Rat-Neu + pLNCX-B7.1 + pLNCX-4-1Bblig |
| 7. | pLNCX-Rat-Neu + pLNCX-B7.2 + pLNCX-4-1Bblig |

Spontaneous FVB/N-TgN (MMTVneu) mammary tumor cells from aged mice appeared as dorsal masses that were removed by sterile dissection from euthanized mice, minced and filtered through a cell strainer to obtain a single-cell suspension. The mammary tumor cells were washed in sterile PBS and adjusted to $2\times10^6/100$ µl for subcutaneous challenge as described above. Typically, tumors appeared in the adoptive recipient animals within 3-4 weeks, at which time tumor surface area measurements of the length and width of the tumor mass in each animal were commenced at 48 h intervals. When the first mouse in a treatment group presented with a tumor having an approximate surface area (length×width) of 200 mm$^2$, animals in that group were euthanized, spleens harvested for flow immunocytofluorimetry as described below in Example 4, and sera were collected by cardiac puncture.

Example 3

Detection Of Specific In Vivo Induction Of Antibodies By Surface Receptor Antigen DNA Vaccine This Example presents an antigen-capture enzyme-linked immunosorbent assay (ELISA) for detection of SRA specific antibodies in the sera of mice immunized with DNA vaccines of the present invention as described in Example 2. The assay involves capturing SRA molecules (in this example the rat Neu protein) using a solid-phase immobilized monoclonal antibody specific for the SRA, and then assaying immune sera from vaccinated animals for the presence of detectable antibodies able to bind the captured SRA.

As a source of rat Neu protein, $10^7$ DHFRG8 cells (ATCC, Rockville, Md.) propagated under culture conditions as specified by the supplier were lysed on ice in 1 ml of lysis buffer (10 mM Tris, 150 mM NaCl, 0.2% Triton X-100 (#A-4529, Sigma, St. Louis, Mo.), 0.2 mg/ml aprotinin (Sigma), 0.2M benzamidine (Sigma), and 0.2M PMSF (Sigma)) and vortexed every 10 minutes for 1 hour. DHFRG8 lysates were clarified by centrifugation to remove insoluble material and the supernatant was collected, assayed for protein content using a Coomassie blue reagent Protein Assay kit (BioRad, Richmond, Calif.), and stored in aliquots at −70° C. until use.

Blood samples were obtained by retro-orbital bleed of FVB/N-TgN (MMTVneu) mice prior to immunization with SRA vaccines as described in Example 2, one week after the booster vaccination, and by cardiac puncture 6-8 weeks after the booster immunization. Sera were prepared and stored at −20° C. until they were analyzed by antibody-capture ELISA for the presence of anti-Rat Neu antibodies. For the ELISA, 96-well plates were coated with 2.5 µg/ml of murine monoclonal antibody specific for rat c-neu (Ab-1, Oncogene Research Products, Cambridge, Mass.) in 50 µl/well of carbonate buffer overnight at 4° C. The plates were incubated with a blocking buffer (PBS+1% bovine serum albumin (BSA, Sigma)) for 4 hours at room temperature and washed 5 times using an ELISA plate washer (BioRad model 1575, Richmond, Calif.) with PBS+0.1% Tween-20 (Sigma). Rows of the 96-well plates were alternatively coated with PBS+1% BSA or with 50 µl/well of DHFRG8 cell lysate (prepared as described above) adjusted to a protein concentraion of 100

μg/ml, and incubated overnight at 4° C. After 5 washes, the plates were incubated with 2-fold serial dilutions of the immune or preimmune serum samples in dilution buffer (PBS, 1% BSA, 1% fetal calf serum (FCS, Gemini Bio Products, Calabasas, Calif.) containing 0.1 M NaN$_3$ (Sigma) and 25 μg/ml carrier mouse immunoglobulins (Organon Teknika, Durham, N.C.) for 1 hour at room temperature. After 5 washes, specifically bound antibodies were detected with horseradish-conjugated goat anti-mouse IgG (Amersham Life Science, Inc., Arlington Heights, Ill.), diluted 1:5000 in PBS +1% BSA, for 45 min at room temperature. After an additional 5 washes, the reactions were developed with TMB substrate buffer (Kirkegaard & Perry Laboratories, Gaithersburg, Md.) and read at 450 nm on a V-max ELISA reader (Molecular Devices, Inc., Sunnyvale, Calif.).

Representative antigen-capture ELISA data are presented in FIG. 1. Preimmune sera from animals in every treatment group exhibited only background Neu binding as evidenced by optical density (OD) levels. Sera from animals of group 2, which were vaccinated only with an SRA (pLNCX-Rat-Neu) encoding construct contained only weakly reactive quantities of anti-Neu antibodies, and were only marginally more reactive than sera from animals of group 1, which were immunized with the unmodified pLNCX plasmid, or those of group 4, which were vaccinated with the combination of pLNCX, pLNCX-Rat-Neu and pLNCX-B7.2. The group 4 results are not inconsistent with reported down-regulation of lymphocyte activation involving CD86/B7.2 under certain conditions (see, e.g., Linsley et al, 1993 *J. Immunol.* 150:3161; Greene et al., 1996 *J. Biol. Chem.* 271:26762; Linsley et al., 1994 *Immunity* 1:793; and references cited therein). In contrast, sera from the animals of groups 3 and 5-7, which were vaccinated with constructs encoding the SRA and one (groups 3, 5) or more (groups 6, 7) IRAM all contained significantly elevated levels of anti-Neu antibodies.

Example 4

Flow Cytometric Analysis Of Splenocytes From Animals Immunized With Surface Receptor Antigen DNA Vaccines Spleens were harvested from tumor bearing mice following treatments as described above in Example 2. The spleens were minced and filtered through a cell strainer to obtain single-cell splenocyte suspensions (Mishell and Shigii (eds.) *Selected Methods in Cellular Immunology*, 1979 Freeman Publishing, San Francisco, Calif.). To obtain purified T cells, the splenocyte suspensions were purified by density sedimentation using Lympholyte M (Cedarlane/Accurate Laboratories, Westbury, N.Y.) according to the manufacturer's instructions. The ratio of T lymphocytes to B lymphocytes was examined by staining lymphocyte suspensions with a fluorescein isothiocyanate (FITC) conjugated murine T cell-specific monoclonal antibody (mAb) (anti-mouse CD3e clone 145-2C11, PharMingen, San Diego, Calif.) and an R-phycoerythrin (R-PE) conjugated murine B cell-specific mAb (anti-mouse CD45R/B220 clone RA3-6B2, also PharMingen). The ratio of CD8+ and CD4+ T cells was examined by staining with FITC anti-mouse CD4 (L3T4) mAb clone Rm4-5 (PharMingen) and R-PE anti-mouse CD8a (Ly-2) mAb clone 53-6.7 (PharMingen).

Briefly, splenocytes ($1 \times 10^6$ cells) were washed and incubated with mAbs at 10 μg/ml in 0.1 ml of staining medium (Dulbeccos Modified Eagle Medium (DMEM, GibcoBRL, Life Technologies, Grand Island, N.Y.) supplemented with 10% FCS, 10 mM EDTA (GibcoBRL), 10 mM Hepes (Sigma) and 0.1% NaN$_3$ (Sigma)) for 1 hour at 4° C. After washing, cells were fixed in 2% formaldehyde (diluted from ultrapure 16% formaldehyde stock solution, Polysciences, Inc., Warrington, Pa.). All flow cytometric analyses were conducted using a FACScan flow cytoflourimeter (Becton Dickinson, Mountain View, Calif.) gated to analyze lymphocytes according to light scattering properties, according to the manufacturer's recommendations.

Figure 2:
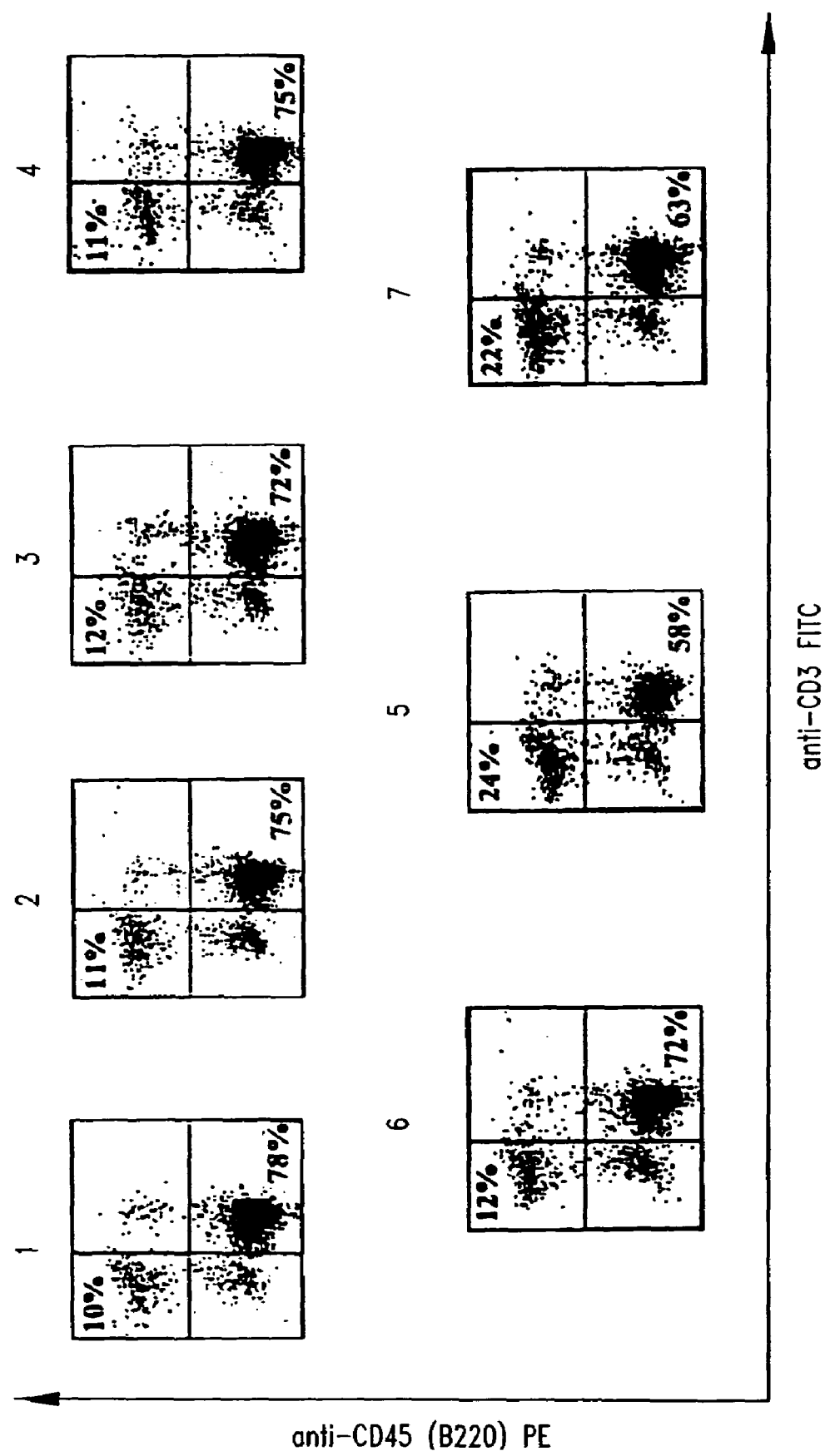

FIG. 2 shows representative immunocytofluorimetry data depicting the splenic T:B lymphocyte ratios in mice from the vaccine treatment groups of Example 2, with the numeric percentages in the upper left and lower right quadrants of each scatter plot indicating the proportion, respectively, of gated cells staining positively for the CD45 (B220) B cell marker and the CD3 T cell marker. As indicated in FIG. 2, in this tumor-burdened murine model spleen T cells profoundly outnumbered spleen B cells in the control treatment group (pLNCX, group 1) and in treatment groups 2-4 and 6. In treatment groups 5 (pLNCX+pLNCX-Rat-Neu+pLNCX-4-1Bblig) and 7 (pLNCX+pLNCX-Rat-Neu+pLNCX-B7.2+pLNCX-4-1Bblig), by contrast, the relative representation of spleen B cells increased significantly.

Example 5

Figure 3:
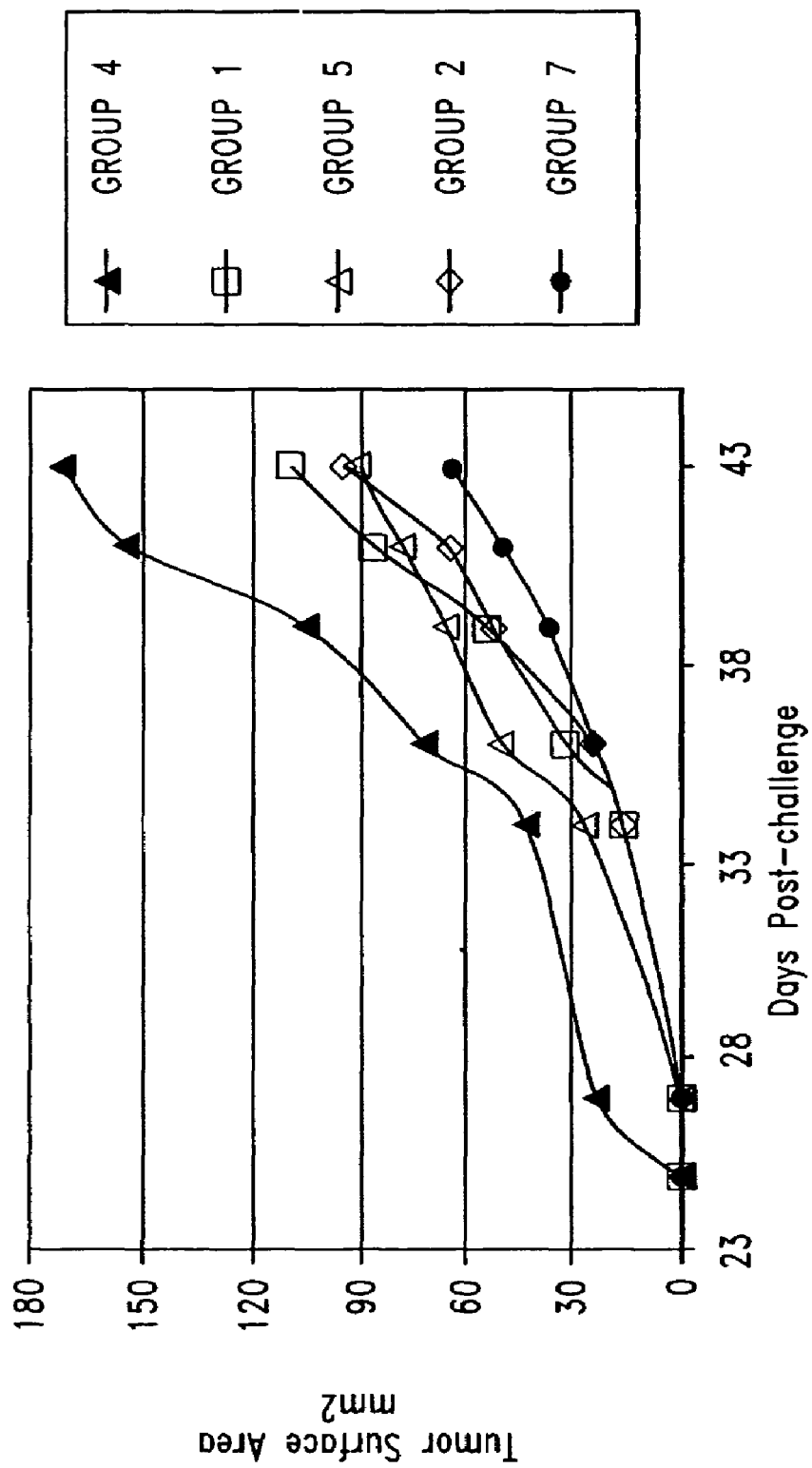

Impaired Tumor Growth In Animals Immunized With Surface Receptor Antigen DNA Vaccine Growth of adoptively transferred FVB/N-TgN (MMTV-neu) mammary tumor cells from aged mice in young FVB/N-TgN (MMTVneu) mice was monitored. Animal treatment groups, tumor inoculations and tumor mass surface area determinations were as described above in Example 2. Data from a representative experiment are presented in FIG. 3. Tumor surface area increased as a function of time in animals of all treatment groups assayed (Groups 1, 2, 4, 5, 7), however, an impaired growth rate and a significantly decreased tumor burden were apparent in animals immunized with a SRA/IRAM encoding DNA vaccine (Group 7: pLNCX+pLNCX-Rat-Neu+pLNCX-B7.2+pLNCX-4-1Bblig). At 35 days post-injection of tumor cells, 2 of 6 mice in Group 7 had tumors classified as small (mean surface area=32 mm2), compared to tumors designated as of intermediate size in Group 1 (4/4 mice, mean s.a.=53 mm$^2$), Group 2 (5/6 mice, mean s.a.=52 mm$^2$) and Group 5 (4/6 mice, mean s.a.=65 mm$^2$), and those of Group 4 were designated large (6/6, mean s.a.=105 mm$^2$). As noted above for Example 3, these group 4 results also are not inconsistent with reported down-regulation of lymphocyte activation involving CD86/B7.2 under certain conditions (see, e.g., Linsley et al, 1993 *J. Immunol.* 150:3161; Greene et al., 1996 *J. Biol.Chem.* 271:26762; Linsley et al., 1994 *Immunity* 1:793; and references cited therein), and thus may illustrate contemplated uses of the invention vaccines, e.g., for suppressing SRA specific responses as described above.

We claim:

1. A composition for eliciting antibodies specific for a cell surface receptor antigen, comprising:
   a) a first recombinant expression construct containing at least one promoter operably linked to a nucleic acid sequence encoding a cell surface receptor antigen, wherein the cell surface receptor antigen is selected from the group consisting of HER1, HER2, HER3 and HER4;
   b) a second recombinant expression construct containing at least one promoter operably linked to a nucleic acid sequence encoding a first immune response altering molecule wherein said first immune response altering molecule comprises 4-1BB-ligand; and
   c) a nucleic acid sequence encoding a second immune response altering molecule selected from the group consisting of CD80/B7.1 and CD86/B7.2.

2. The composition of claim 1, wherein the second recombinant expression construct comprises the nucleic acid sequence encoding the second immune response altering molecule.

3. The composition of claim 1, further comprising a third recombinant expression construct comprising the nucleic acid sequence encoding the second immune response altering molecule.

4. The composition of claim 1, wherein the cell surface receptor antigen is HER2.

5. The composition of claim 1, wherein the second immune response altering molecule is CD80/B7.1

6. The composition of claim 1, wherein the second immune response altering molecule is CD86/B7.2.

7. The composition of claim 2, wherein the second recombinant expression construct further comprises an internal ribosome binding site (IRES) operably inserted between the 4-1BB-ligand and the second immune response molecule.

8. The composition of claim 1, wherein the at least one promoter in the second recombinant expression construct is the cytomegalovirus (CMV) promoter.

9. The composition of claim 1, further comprising a pharmaceutically acceptable carrier for parenteral administration selected from the group consisting of water, saline, alcohol, a fat, a wax or a buffer.

10. The composition of claim 9, wherein the recombinant constructs comprise from 0.01% to 1% of the total weight of the composition.

11. The composition of claim 1, wherein the composition further comprises at least one cytokine, or nucleic acid encoding at least one cytokine selected from the group consisting of interleukin 4 (IL-4), interleukin-12 (IL- 12), interleukin-17 (IL- 17), and interferon-gamma (IFN-gamma).

* * * * *

UNITED STATES PATENT AND TRADEMARK OFFICE
CERTIFICATE OF CORRECTION

PATENT NO. : 7,547,681 B2
APPLICATION NO. : 10/762128
DATED : June 16, 2009
INVENTOR(S) : Scholler et al.

It is certified that error appears in the above-identified patent and that said Letters Patent is hereby corrected as shown below:

Column 1

Line 11, before the section "Technical Field" please add the following Government Rights section heading and paragraph:

GOVERNMENT RIGHTS

This invention was made with government support under grant number(s) CA083636 and CA098008, awarded by the National Institutes of Health. The government has certain rights in the invention.

Signed and Sealed this

Twenty-seventh Day of July, 2010

David J. Kappos
*Director of the United States Patent and Trademark Office*